United States Patent
Ganz et al.

(10) Patent No.: US 7,534,764 B2
(45) Date of Patent: May 19, 2009

(54) COMPETITIVE REGULATION OF HEPCIDIN MRNA BY SOLUBLE AND CELL-ASSOCIATED HEMOJUVELIN

(75) Inventors: Tomas Ganz, Los Angeles, CA (US); Lan Lin, Los Angeles, CA (US); Yigal P. Goldberg, Vancouver (CA)

(73) Assignees: The Regents of the University of California, Oakland, CA (US); Xenon Pharmaceuticals, Inc., Burnaby, British Columbia (CA)

( * ) Notice: Subject to any disclaimer, the term of this patent is extended or adjusted under 35 U.S.C. 154(b) by 302 days.

(21) Appl. No.: 11/427,095

(22) Filed: Jun. 28, 2006

(65) Prior Publication Data

US 2007/0004618 A1 Jan. 4, 2007

Related U.S. Application Data

(60) Provisional application No. 60/694,676, filed on Jun. 29, 2005.

(51) Int. Cl.
*A61K 38/00* (2006.01)
(52) U.S. Cl. ...................................................... 514/12
(58) Field of Classification Search ..................... 514/12
See application file for complete search history.

(56) References Cited

U.S. PATENT DOCUMENTS

2006/0073497 A1 4/2006 Goldberg et al.
2007/0166711 A1 7/2007 Samuels et al.

FOREIGN PATENT DOCUMENTS

WO 2004092405 A2 10/2004

OTHER PUBLICATIONS

George Papanikolaou et al., "Mutations in HFE2 Cause Iron Overload in Chromosome 1q-linked Juvenile Hemochromatosis", Nature Genetics Advance Online Publication, 2003 Nature Publishing Group; http://www.nature.com/naturegenetics, pp. 1-6.
George Papanikolaou et al., "Hepcidin in Iron Overload Disorders", Blood, 15 May 2005, vol. 105, No. 10, pp. 4103-4105.

*Primary Examiner*—Maryam Monshipouri
(74) *Attorney, Agent, or Firm*—Suzannah K. Sundby, Esq.; Smith, Gambrell & Russell, LLP

(57) ABSTRACT

Disclosed herein are hemojuvelin-specific siRNAs that vary hemojuvelin mRNA concentration. Also disclosed herein, GPI-hemojuvelin positively regulated hepcidin mRNA expression, independently of the IL-6 pathway, whereas soluble hemojuvelin (s-hemojuvelin) suppressed hepcidin mRNA expression in primary human hepatocytes in a log-linear dosedependent manner. Disclosed are compositions and methods for modulating diseases of iron metabolism and hepcidin expression or hepcidin levels.

4 Claims, 11 Drawing Sheets

SEQUENCE LISTING

```
<160> NUMBER OF SEQ ID NOS: 20

<210> SEQ ID NO 1
<211> LENGTH: 368
<212> TYPE: PRT
<213> ORGANISM: Artificial
<220> FEATURE:
<223> OTHER INFORMATION: Human recombinant soluble hemojuvelin

<400> SEQUENCE: 1

Gln Cys Lys Ile Leu Arg Cys Asn Ala Glu Tyr Val Ser Ser Thr Leu
1               5                   10                  15

Ser Leu Arg Gly Gly Gly Ser Ser Gly Ala Leu Arg Gly Gly Gly Gly
            20                  25                  30

Gly Gly Arg Gly Gly Gly Val Gly Ser Gly Gly Leu Cys Arg Ala Leu
        35                  40                  45

Arg Ser Tyr Ala Leu Cys Thr Arg Arg Thr Ala Arg Thr Cys Arg Gly
    50                  55                  60

Asp Leu Ala Phe His Ser Ala Val His Gly Ile Glu Asp Leu Met Ile
65                  70                  75                  80

Gln His Asn Cys Ser Arg Gln Gly Pro Thr Ala Pro Pro Pro Pro Arg
                85                  90                  95

Gly Pro Ala Leu Pro Gly Ala Gly Ser Gly Leu Pro Ala Pro Asp Pro
            100                 105                 110

Cys Asp Tyr Glu Gly Arg Phe Ser Arg Leu His Gly Arg Pro Pro Gly
        115                 120                 125

Phe Leu His Cys Ala Ser Phe Gly Asp Pro His Val Arg Ser Phe His
    130                 135                 140

His His Phe His Thr Cys Arg Val Gln Gly Ala Trp Pro Leu Leu Asp
145                 150                 155                 160

Asn Asp Phe Leu Phe Val Gln Ala Thr Ser Ser Pro Met Ala Leu Gly
                165                 170                 175

Ala Asn Ala Thr Ala Thr Arg Lys Leu Thr Ile Ile Phe Lys Asn Met
            180                 185                 190

Gln Glu Cys Ile Asp Gln Lys Val Tyr Gln Ala Glu Val Asp Asn Leu
        195                 200                 205

Pro Val Ala Phe Glu Asp Gly Ser Ile Asn Gly Gly Asp Arg Pro Gly
    210                 215                 220

Gly Ser Ser Leu Ser Ile Gln Thr Ala Asn Pro Gly Asn His Val Glu
```

```
                225                 230                 235                 240
Ile Gln Ala Ala Tyr Ile Gly Thr Thr Ile Ile Arg Gln Thr Ala
                245                 250                 255
Gly Gln Leu Ser Phe Ser Ile Lys Val Ala Glu Asp Val Ala Met Ala
                260                 265                 270
Phe Ser Ala Glu Gln Asp Leu Gln Leu Cys Val Gly Gly Cys Pro Pro
            275                 280                 285
Ser Gln Arg Leu Ser Arg Ser Glu Arg Asn Arg Gly Ala Ile Thr
            290                 295                 300
Ile Asp Thr Ala Arg Arg Leu Cys Lys Glu Gly Leu Pro Val Glu Asp
305                 310                 315                 320
Ala Tyr Phe His Ser Cys Val Phe Asp Val Leu Ile Ser Gly Asp Pro
                325                 330                 335
Asn Phe Thr Val Ala Ala Gln Ala Ala Leu Glu Asp Ala Arg Ala Phe
                340                 345                 350
Leu Pro Asp Leu Glu Lys Leu His Leu Phe Pro Ser Asp Ala Gly Val
                355                 360                 365

<210> SEQ ID NO 2
<211> LENGTH: 21
<212> TYPE: DNA
<213> ORGANISM: Artificial
<220> FEATURE:
<223> OTHER INFORMATION: siRNA duplex targeting human hemojuvelin mRNA

<400> SEQUENCE: 2
aactctaagc actctcactc t                                          21

<210> SEQ ID NO 3
<211> LENGTH: 21
<212> TYPE: DNA
<213> ORGANISM: Artificial
<220> FEATURE:
<223> OTHER INFORMATION: siRNA duplex targeting human hemojuvelin mRNA

<400> SEQUENCE: 3
aaccattgat actgccagac g                                          21

<210> SEQ ID NO 4
<211> LENGTH: 21
<212> TYPE: DNA
<213> ORGANISM: Artificial
<220> FEATURE:
<223> OTHER INFORMATION: siRNA duplex targeting human hemojuvelin mRNA

<400> SEQUENCE: 4
aagtttagag gtcatgaagg t                                          21

<210> SEQ ID NO 5
<211> LENGTH: 21
<212> TYPE: DNA
<213> ORGANISM: Artificial
<220> FEATURE:
<223> OTHER INFORMATION: siRNA duplex targeting human hemojuvelin mRNA

<400> SEQUENCE: 5
aaagctacaa attcttcaca c                                          21

<210> SEQ ID NO 6
<211> LENGTH: 19
<212> TYPE: DNA
<213> ORGANISM: Artificial
```

```
<220> FEATURE:
<223> OTHER INFORMATION: siRNA negative control for targeting human
      hemojuvelin mRNA

<400> SEQUENCE: 6
gcgcgctttg taggattcg                                               19

<210> SEQ ID NO 7
<211> LENGTH: 21
<212> TYPE: DNA
<213> ORGANISM: Artificial
<220> FEATURE:
<223> OTHER INFORMATION: siRNA negative control for targeting human
      hemojuvelin mRNA.

<400> SEQUENCE: 7
aattctccga acgtgtcacg t                                            21

<210> SEQ ID NO 8
<211> LENGTH: 20
<212> TYPE: DNA
<213> ORGANISM: Artificial
<220> FEATURE:
<223> OTHER INFORMATION: forward primer qRT-PCR for hepcidin

<400> SEQUENCE: 8
cacaacagac gggacaactt                                              20

<210> SEQ ID NO 9
<211> LENGTH: 20
<212> TYPE: DNA
<213> ORGANISM: Artificial
<220> FEATURE:
<223> OTHER INFORMATION: reverse primer qRT-PCR for hepcidin

<400> SEQUENCE: 9
cgcagcagaa aatgcagatg                                              20

<210> SEQ ID NO 10
<211> LENGTH: 22
<212> TYPE: DNA
<213> ORGANISM: Artificial
<220> FEATURE:
<223> OTHER INFORMATION: forward primer for qRT-PCR human hemojuvelin

<400> SEQUENCE: 10
ctcttagctc cactcctttc tg                                           22

<210> SEQ ID NO 11
<211> LENGTH: 22
<212> TYPE: DNA
<213> ORGANISM: Artificial
<220> FEATURE:
<223> OTHER INFORMATION: reverse primer for qRT-PCR human hemojuvelin

<400> SEQUENCE: 11
gccctgcttc ctttaatgat tc                                           22

<210> SEQ ID NO 12
<211> LENGTH: 19
<212> TYPE: DNA
<213> ORGANISM: Artificial
<220> FEATURE:
<223> OTHER INFORMATION: forward primer for qRT-PCR human G3PD

<400> SEQUENCE: 12
```
tggtatcgtg gaaggactc         19

<210> SEQ ID NO 13
<211> LENGTH: 19
<212> TYPE: DNA
<213> ORGANISM: Artificial
<220> FEATURE:
<223> OTHER INFORMATION: reverse primer for qRT-PCR human G3PD

<400> SEQUENCE: 13
agtagaggca gggatgatg         19

<210> SEQ ID NO 14
<211> LENGTH: 18
<212> TYPE: DNA
<213> ORGANISM: Artificial
<220> FEATURE:
<223> OTHER INFORMATION: forward primer for qRT-PCR human beta-actin

<400> SEQUENCE: 14
atcgtgcgtg acattaag         18

<210> SEQ ID NO 15
<211> LENGTH: 18
<212> TYPE: DNA
<213> ORGANISM: Artificial
<220> FEATURE:
<223> OTHER INFORMATION: reverse primer for qRT-PCR human beta-actin

<400> SEQUENCE: 15
attgccaatg gtgatgac         18

<210> SEQ ID NO 16
<211> LENGTH: 18
<212> TYPE: DNA
<213> ORGANISM: Artificial
<220> FEATURE:
<223> OTHER INFORMATION: forward primer for qRT-PCR human CEBPdelta

<400> SEQUENCE: 16
caacgaccca tacctcag         18

<210> SEQ ID NO 17
<211> LENGTH: 18
<212> TYPE: DNA
<213> ORGANISM: Artificial
<220> FEATURE:
<223> OTHER INFORMATION: reverse primer for qRT-PCR human CEBPdelta

<400> SEQUENCE: 17
ggtaagtcca ggctgtag         18

<210> SEQ ID NO 18
<211> LENGTH: 16
<212> TYPE: PRT
<213> ORGANISM: Artificial
<220> FEATURE:
<223> OTHER INFORMATION: human antigen anti-G3pep2-2

<400> SEQUENCE: 18

Cys Arg Gly Asp Leu Ala Phe His Ser Ala Val His Gly Ile Glu Asp
 1               5                  10                  15

<210> SEQ ID NO 19
<211> LENGTH: 16
<212> TYPE: PRT

-continued

```
<213> ORGANISM: Artificial
<220> FEATURE:
<223> OTHER INFORMATION: human antigen anti-G3pep2-3

<400> SEQUENCE: 19

Cys Asp Tyr Glu Gly Arg Phe Ser Arg Leu His Gly Arg Pro Pro Gly
1               5                   10                  15

<210> SEQ ID NO 20
<211> LENGTH: 328
<212> TYPE: PRT
<213> ORGANISM: Artificial
<220> FEATURE:
<223> OTHER INFORMATION: soluble mouse hemojuvelin protein sequence
      encoded by pRRL-Hjv-FUR

<400> SEQUENCE: 20

Met Gly Gln Ser Pro Ser Pro Arg Ser Pro His Gly Ser Pro Pro Thr
1               5                   10                  15

Leu Ser Thr Leu Thr Leu Leu Leu Leu Cys Gly Gln Ala His Ser
                20                  25                  30

Gln Cys Lys Ile Leu Arg Cys Asn Ala Glu Tyr Val Ser Ser Thr Leu
            35                  40                  45

Ser Leu Arg Gly Gly Gly Ser Pro Asp Thr Pro Arg Gly Gly Gly Arg
    50                  55                  60

Gly Gly Leu Ala Ser Gly Gly Leu Cys Arg Ala Leu Arg Ser Tyr Ala
65                  70                  75                  80

Leu Cys Thr Arg Arg Thr Ala Arg Thr Cys Arg Gly Asp Leu Ala Phe
                85                  90                  95

His Ser Ala Val His Gly Ile Glu Asp Leu Met Ile Gln His Asn Cys
            100                 105                 110

Ser Arg Gln Gly Pro Thr Ala Pro Pro Ala Arg Gly Pro Ala Leu
        115                 120                 125

Pro Gly Ala Gly Pro Ala Pro Leu Thr Pro Asp Pro Cys Asp Tyr Glu
    130                 135                 140

Ala Arg Phe Ser Arg Leu His Gly Arg Ala Pro Gly Phe Leu His Cys
145                 150                 155                 160

Ala Ser Phe Gly Asp Pro His Val Arg Ser Phe His Asn Gln Phe His
                165                 170                 175

Thr Cys Arg Val Gln Gly Ala Trp Pro Leu Leu Asp Asn Asp Phe Leu
            180                 185                 190

Phe Val Gln Ala Thr Ser Ser Pro Val Ser Ser Gly Ala Asn Ala Thr
        195                 200                 205

Thr Ile Arg Lys Ile Thr Ile Ile Phe Lys Asn Met Gln Glu Cys Ile
    210                 215                 220

Asp Gln Lys Val Tyr Gln Ala Glu Val Asp Asn Leu Pro Ala Ala Phe
225                 230                 235                 240

Glu Asp Gly Ser Ile Asn Gly Gly Asp Arg Pro Gly Gly Ser Ser Leu
                245                 250                 255

Ser Ile Gln Thr Ala Asn Leu Gly Ser His Val Glu Ile Arg Ala Ala
            260                 265                 270

Tyr Ile Gly Thr Thr Ile Ile Ile Arg Gln Thr Ala Gly Gln Leu Ser
        275                 280                 285

Phe Ser Ile Arg Val Ala Glu Asp Val Ala Arg Ala Phe Ser Ala Glu
    290                 295                 300

Gln Asp Leu Gln Leu Cys Val Gly Gly Cys Pro Pro Ser Gln Arg Leu
305                 310                 315                 320
```

```
Ser Arg Ser Glu Arg Asn Arg Arg
            325
```

COMPETITIVE REGULATION OF HEPCIDIN MRNA BY SOLUBLE AND CELL-ASSOCIATED HEMOJUVELIN

CROSS-REFERENCE TO RELATED APPLICATIONS

This application claims the benefit of U.S. Provisional Patent Application Ser. No. 60/694,676, filed 29 Jun. 2005, naming Thomas Ganz and Lan Lin as inventors, which is herein incorporated by reference in its entirety.

BACKGROUND OF THE INVENTION

1. Field of the Invention

The present invention relates to diseases of iron metabolism, hepcidin and hemojuvelin.

2. Description of the Related Art

Various diseases of iron metabolism are known in the art and include hemochromatosis, ferroportin mutation hemochromatosis, transferrin receptor 2 mutation hemochromatosis, juvenile hemochromatosis, neonatal hemochromatosis, hepcidin deficiency, transfusional iron overload, thalassemia, thalassemia intermedia, alpha thalassemia, sideroblastic anemia, porphyria, porphyria cutanea tarda, African iron overload, hyperferritinemia, ceruloplasmin deficiency, atransferrinemia, congenital dyserythropoietic anemia, anemia of chronic disease, anemia, hypochromic microcytic anemia, iron-deficiency anemia, conditions with hepcidin excess, Friedreich ataxia, gracile syndrome, Hallervorden-Spatz disease, Wilson's disease, pulmonary hemosiderosis, hepatocellular carcinoma, cancer, hepatitis, cirrhosis of liver, pica, chronic renal failure, insulin resistance, diabetes, atherosclerosis, neurodegenerative disorders, multiple sclerosis, Parkinson's Disease, Huntington's Disease, Alzheimer's Disease.

Juvenile hemochromatosis (JH) is an early-onset inherited disorder of iron overload. Two phenotypically very similar forms have been recently characterized, one due to the homozygous disruption of the HJV gene encoding a protein named hemojuvelin, and the other due to the homozygous disruption of the HAMP gene encoding hepcidin. See Papanikolaou, G, et al. (2004) Nat. Genet. 36:77-82. Hepcidin is a key iron-regulatory peptide hormone which controls extracellular iron concentration by regulating the major iron flows into plasma, and normally constrains intestinal iron absorption. See Ganz, T. (2005) Best Pract. Res. Clin. Haematol. 18:171-182. Although a few mutated forms of juvenile hemochromatosis gene (HFE2A) have been identified and may be suitable for detecting the mutations, no suitable therapeutic has been identified and shown to have a therapeutic effect. See Samuels, et al. WO 2004092405.

Anemia of chronic disease (alternatively known as anemia of inflammation) is another disease of iron metabolism due to the excessive production of the iron-regulatory hormone hepcidin. See Rivera, S., et al. (2005) Blood 105:1797-1802; Nemeth, E., et al. (2004) J. Clin. Invest 113:1271-1276; Roy & Andrews (2005) Curr. Opin. Hematol. 12:107-111; Fleming & Sly (2001) PNAS USA 98:8160-8162; and Weiss & Goodnough (2005) N. Engl. J. Med. 352:1011-1023. Anemia of chronic disease is a condition associated with inflammatory diseases including rheumatological disorders, inflammatory bowel diseases, chronic infections, chronic renal diseases, as well as with malignant disorders including various forms of cancer, lymphomas and multiple myeloma, and the like.

In anemia of chronic disease (anemia of inflammation) the production of hepcidin is stimulated by various cytokines including interleukin-6. Hepcidin acts by binding to ferroportin, the sole known cellular iron exporter, and inducing its degradation. Excess hepcidin causes the loss of ferroportin from the surfaces of macrophages engaged in the recycling of iron from senescent red cells. See Nemeth, E., et al. (2004) Science 306:2090-2093. As a result, iron is trapped in macrophages and blood iron concentrations decrease, restricting the flow of iron to the bone marrow, and thus slowing the production of hemoglobin and consequently decreasing the production of red blood cells. See Rivera, S., et al. (2005). Synthetic hepcidin causes rapid dose-dependent hypoferremia and is concentrated in ferroportin-containing organs, Blood (2005). Unfortunately, suitable and effective therapies for anemia of chronic disease are limited. Specifically, the three main therapies are based on (1) treating the underlying disease which is usually not possible, otherwise this diagnosis would not exist, (2) erythropoietin administration which is effective in only about 50% of all the patients and is associated with undesirable side effects, and (3) transfusions which are undesirable due to contamination, infection and iron overload.

Thus, a need still exists for compositions and methods for treating diseases of iron metabolism, such as juvenile hemochromatosis and anemia of chronic disease.

SUMMARY OF THE INVENTION

The present invention provides compositions and methods for modulating hepcidin and disease of iron metabolism.

In some embodiments, the present invention provides a method of treating, preventing, modulating, or attenuating a disease of iron metabolism in a subject which comprises administering to the subject a therapeutically effective amount of a least one soluble hemojuvelin protein. In some embodiments, the soluble hemojuvelin protein lacks a glycophosphatidylinositol anchor. In some embodiments, the soluble hemojuvelin protein is a polypeptide consisting of at least 6 consecutive amino acid residues of SEQ ID NO:1. In some embodiments, the polypeptide consists of at least 20 consecutive amino acid residues of SEQ ID NO:1. In some embodiments, the polypeptide consists of at least 50 consecutive amino acid residues of SEQ ID NO:1. In some embodiments, the polypeptide consists of SEQ ID NO:1. In some embodiments, the disease of iron metabolism is anemia of chronic disease also sometimes referred to as anemia of inflammation.

In some embodiments, the present invention provides a method of modulating hepcidin production or hepcidin levels in a subject which comprises administering to the subject a membrane-associated GPI-linked hemojuvelin or a soluble hemojuvelin protein. In some embodiments, the soluble hemojuvelin protein lacks a glycophosphatidylinositol anchor. In some embodiments, the soluble hemojuvelin protein is a polypeptide consisting of at least 6 consecutive amino acid residues of SEQ ID NO:1. In some embodiments, the polypeptide consists of at least 20 consecutive amino acid residues of SEQ ID NO:1. In some embodiments, the polypeptide consists of at least 50 consecutive amino acid residues of SEQ ID NO:1. In some embodiments, administration of the membrane-associated GPI-linked hemojuvelin increases hepcidin production. In some embodiments, administration of the soluble hemojuvelin protein decreases hepcidin production.

In some embodiments, the present invention provides a method of treating, preventing, modulating, or attenuating a disease of iron deficiency in a subject which comprises modulating hepcidin production or hepcidin levels in the subject which comprises administering to the subject a membrane-associated GPI-linked hemojuvelin or a soluble hemojuvelin protein. In some embodiments, the soluble hemojuvelin protein lacks a glycophosphatidylinositol anchor. In some embodiments, the soluble hemojuvelin protein is a polypeptide consisting of at least 6 consecutive amino acid residues of SEQ ID NO:1. In some embodiments, the polypeptide consists of at least 20 consecutive amino acid residues of SEQ ID NO:1. In some embodiments, the polypeptide consists of at least 50 consecutive amino acid residues of SEQ ID NO:1. In some embodiments, administration of the membrane-associated GPI-linked hemojuvelin increases hepcidin production. In some embodiments, administration of the soluble hemojuvelin protein decreases hepcidin production.

In some embodiments, the present invention provides a purified polypeptide consisting of at least 6 consecutive amino acid residues of SEQ ID NO:1. In some embodiments, the polypeptide consists of at least 20 consecutive amino acid residues of SEQ ID NO:1. In some embodiments, the polypeptide consists of at least 50 consecutive amino acid residues of SEQ ID NO:1.

In some embodiments, the present invention provides a pharmaceutical composition comprising at least one purified polypeptide of the present invention and a pharmaceutically acceptable carrier. In some embodiments, the purified polypeptide consists of at least 6 consecutive amino acid residues of SEQ ID NO:1. In some embodiments, the polypeptide consists of at least 20 consecutive amino acid residues of SEQ ID NO:1. In some embodiments, the polypeptide consists of at least 50 consecutive amino acid residues of SEQ ID NO:1.

In some embodiments, the present invention provides a method for monitoring or diagnosing a disease of iron metabolism in a subject comprising assaying the amount of membrane-associated GPI-linked hemojuvelin in biopsy material or by non-invasive means in human subjects, the concentration of soluble hemojuvelin protein in blood, serum or plasma, or both in the subject and determining whether the amount is normal or abnormal.

DESCRIPTION OF THE DRAWINGS

This invention is further understood by reference to the drawings wherein:

FIG. 1A is a plot showing a regression line (all HJV siRNAs experiments, R=0.64, with 95% confidence limit) indicates that as HJV/G3PD ratio decreases, there is a corresponding decrease in the hepcidin mRNA/G3PD ratio. Closed symbols represent hemojuvelin siRNAs experiments (■: HJVsi1, ●: HJVsi2, ▼: HJVsi3, ▲: HJVsi4).

FIG. 1B is a plot showing no consistent effect on hepcidin is seen with control siRNAs. Note the larger horizontal scale compared to panel A. Open symbols represent siRNA control experiments (Δ: NCsi1, ○: NCsi2, □: NCsi3).

FIG. 5A shows gels of HEK293 and Hep3B cells transfected with hemojuvelin vector (pcDNA-HJV) in 6-well tissue culture plates and incubated overnight, followed by a 24-hour incubation in serum free medium (2 ml/well) with FAC concentrations ranging from about 0 to about 100 μM. Conditioned cell culture medium (2 ml/sample) was filter-concentrated (5 kD cutoff) and analyzed on a reducing SDS-PAGE/western blot probed with anti-G3pep2-3. In both Hep3B (upper panel) and HEK293 cells (lower panel), the amount of soluble hemojuvelin decreased progressively with increasing FAC concentrations.

FIG. 5B shows gels of Holo- and Apo-transferrin added to pcDNA-HJV transfected HEK293 cells at various ratios to reach a constant total transferrin concentration of 30 μM. Conditioned cell culture medium (2 ml/sample) was extracted by cation exchange and filter-concentrated (5 kD cutoff) before being analyzed on a non-reducing SDS-PAGE/ Western blot probed with Ab112. Lane 1 shows conditioned cell culture medium from pcDNA 3.1 (+) vector transfected HEK293 cells as a negative control. The amount of soluble hemojuvelin decreased progressively with increasing iron saturation of transferrin.

FIG. 10A indicates that regardless of IL-6 treatment (IL-6 untreated: open symbol, dot line; 20 ng/ml IL-6: closed symbol, dashed line), addition of s-hemojuvelin to primary human hepatocyte showed a similar suppression of hepcidin mRNA expression. Hepcidin/β-actin ratio of s-hemojuvelin untreated cells was used as baseline=1 within each experiment (with or without IL-6).

FIG. 10B shows that IL-6 (20 ng/ml) induced hepcidin expression 6 and 16-fold in the hepatocyte cultures from 2 different donors (closed symbols, 0 ng/ml s-hemojuvelin). The addition of s-hemojuvelin significantly lowered hepcidin expression; high dose (about 1000 to about 3000 ng/ml) treatment restored hepcidin expression to a normal or nearly normal level. Cells not treated with s-hemojuvelin or IL-6 in each pair of experiments were used as controls and their hepcidin/β-actin ratio of control cells was set as baseline=1.

In FIG. 11A, light grey color is used to identify transcripts that are absent or marginally detectable in both treated and untreated cells, dark grey designates transcripts that are absent or marginal in either treated or mock-treated cells, and black color indicates transcripts that are present in both treated and mock-treated cells.

In FIG. 11B, the colors are changed to indicate transcripts that are significantly increased (black), unchanged (grey) or decreased (black) with s-hemojuvelin treatment.

DETAILED DESCRIPTION

Figure 1A:
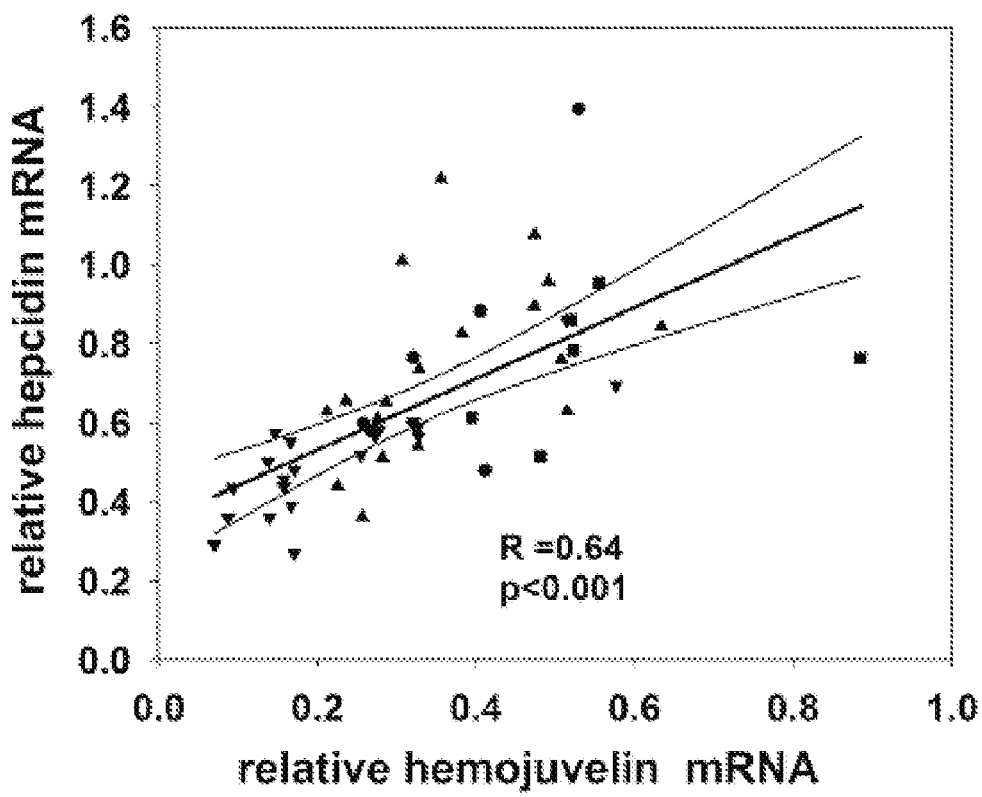
FIGS. 1A and 1B show that suppression of hemojuvelin mRNA results in the suppression of hepcidin mRNA. Each individual point represents an experiment in which Hep3B cells were treated with one of the siRNA preparations overnight, and then incubated for additional 24 hours before mRNA extraction. In each experiment, hemojuvelin and hepcidin mRNA were quantified by real time qRT-PCR and normalized to the housekeeping gene G3PD. Control cells were treated only with transfection reagents and their hemojuvelin/G3PD and hepcidin/G3PD ratios were set as baseline=1.

As provided herein, the expression and regulatory roles of GPI-hemojuvelin and soluble forms of hemojuvelin (s-hemojuvelin) were studied and it was found that, in extracellular iron homeostasis, GPI-hemojuvelin and s-hemojuvelin act as opposing regulators of hepcidin. Therefore, the present invention provides compositions and methods for regulating or modulating hepcidin.

The hemojuvelin (HJV) gene produces multiple alternatively spliced mRNA isoforms. The longest isoform of hemojuvelin mRNA encodes a 426 amino acid protein, which contains a C-terminal putative transmembrane domain characteristic of a glycosylphosphatidylinositol-linked membrane anchor (GPI-anchor). See Niederkofler, V. et al. (2004) J. Neurosci. 24:808-818; and Monnier, P.P., et al. (2002) Nature 419:392-395.

The genetic linkage between juvenile hemochromatosis due to HJV mutations and nearly absent hepcidin excretion in the affected individuals left open the possibility that hemojuvelin, like its congener RgmA, is a developmental factor. See Rajagopalan, S., et al. (2004) Nat. Cell Biol. 6:756-762, which is herein incorporated by reference. RgmA and hemojuvelin are associated with cell membranes but both lack cytoplasmic tails and contain consensus sequences indicating that they are GPI-linked proteins. See Niederkofler, V., et al. (2004) J. Neurosci. 24:808-818, which is herein incorporated by reference. RgmA is involved in neural development through binding to a protein ligand neogenin, a transmembrane receptor. See Rajagopalan, S., et al. (2004) Nat. Cell Biol. 6:756-762, which is herein incorporated by reference. Thus, GPI-linked cell-associated hemojuvelin (GPI-hemojuvelin) may also interact with a similar transmembrane receptor, to stimulate the production of hepcidin.

In principle, the deficiency of hepcidin in subjects having HJV mutations could be due to a developmental defect in hepatocyte function or due to the involvement of hemojuvelin in hepcidin regulation. To establish whether hemojuvelin controlled hepcidin synthesis, a human hepatoma cell line Hep3B was used as a model for in vitro studies. Hep3B cells spontaneously produce hemojuvelin mRNA at a similar concentration as in primary human hepatocytes (data not shown).

As provided herein, Hep3B human hepatocarcinoma cells and HEK293T/17 cells (HEK293) were maintained in Dulbecco's Modified Eagle Medium (DMEM; Invitrogen, Carlsbad, Calif.) supplemented with 10% fetal bovine serum (FBS). Human hepatocytes (Liver Tissue Procurement and Distribution System, Minneapolis, Minn.) were cultured in human hepatocyte maintenance medium (Clonetics, San Diego, Calif.) at 37° C. in 5% humidified $CO_2$. Hepatocytes were treated with purified recombinant s-hemojuvelin

QCKILRCNAEYVSSTLSLRGGGSSGALRGGGGGRGG  (SEQ ID NO:1)

GVGSGGLCRALRSYALCTRRTARTCRGDLAFHSAVHG

IEDLMIQHNCSRQGPTAPPPPRGPALPGAGSGLPAPD

PCDYEGRFSRLHGRPPGFLHCASFGDPHVRSFHHHFH

TCRVQGAWPLLDNDFLFVQATSSPMALGANATATRKL

TIIFKNMQECIDQKVYQAEVDNLPVAFEDGSINGGDR

PGGSSLSIQTANPGNHVEIQAAYIGTTIIIRQTAGQL

SFSIKVAEDVAMAFSAEQDLQLCVGGCPPSQRLSRSE

RNRRGAITIDTARRLCKEGLPVEDAYFHSCVFDVLIS

GDPNFTVAAQAALEDARAFLPDLEKLHLFPSDAGV for 24 hours before harvesting. Human recombinant IL-6 (R&D Systems, Minneapolis, Minn.) was used at 20 ng/ml concentration.

Human serum and plasma were obtained from volunteer donors under an IRB-approved protocol. Frozen normal human liver tissue was obtained from the UCLA Human Tissue Resource Center (Los Angeles, Calif.) under an IRB-approved protocol.

Construction of siRNA

Four siRNA duplexes targeting human hemojuvelin mRNA and one siRNA negative control were constructed using Silencer® siRNA Construction Kit (Ambion, Austin, Tex.) according to the manufacturer's instructions. HJV siRNA targets, commercially available from Dharmacon, Inc., Lafayette, Colo., included:

HJVsi1:   5'-AACTCTAAGCACTCTCACTCT-3'   (SEQ ID NO:2)

HJVsi2:   5'-AACCATTGATACTGCCAGACG-3'   (SEQ ID NO:3)

HJVsi3:   5'-AAGTTTAGAGGTCATGAAGGT-3'   (SEQ ID NO:4)

HJVsi4:   5'-AAAGCTACAAATTCTTCACAC-3'   (SEQ ID NO:5)

A negative control, NCsi1 target: 5'-GCGCGCTTTGTAGGATTCG-3' (SEQ ID NO:6) was used.

The following siRNA negative control duplex were also used: NCsi2: 5'-AATTCTCCGAACGTGTCACGT-3' (SEQ ID NO:7) (Qiagen, Valencia, Calif.) NCsi3: Silencer® Negative Control #2 siRNA (Ambion, Austin, Tex.).

Transfections

In all siRNA treatment experiments, Hep3B cells were seeded at 10% confluence 24 hours before siRNA transfection. Hep3B cells were transfected with 20 nM siRNA duplexes using Oligofectamine Transfection Reagent (Invitrogen, Carlsbad, Calif.) according to manufacturer's protocol for 24 hours, followed by 24-hour treatment with 20 ng/ml human recombinant IL-6 (R&D Systems, Minneapolis, Minn.) or its solvent. In hemojuvelin expression experiments, 24 hours before transfection, Hep3B cells were seeded at 50% confluence and HEK293 cells were seeded at 10% confluence. pcDNA-HJV was generated by cloning full length human HJV cDNA into vector pcDNA3.1 (+) plasmid (Invitrogen, Carlsbad, Calif.). The pcDNA-HJV or the control plasmid vector pcDNA3.1 (+) were transfected using Lipofectamine™ 2000 Transfection Reagent (Invitrogen, Carlsbad, Calif.) according to manufacturer's protocol for 24 hours prior to further treatment.

Recombinant Soluble Hemojuvelin Production and Purification

To express recombinant soluble human hemojuvelin (s-hemojuvelin), a cDNA of human hemojuvelin truncated by 72 nucleotides at the 3' end to remove the transmembrane segment and with an added stop codon, was cloned into BaculoDirect baculovirus expression system (Invitrogen) according to manufacturer's instructions. Culture medium from infected Hi5 insect cell culture was purified by cation exchange chromatography (CM Prep, Biorad, Richmond, Calif.), followed by high performance liquid chromatography on a C4 reverse phase column (Vydac, 214TP54) eluted with an acetonitrile gradient.

RNA Isolation, mRNA Assay and Microarray Analysis

RNA from Hep3B cells and primary human hepatocytes was prepared using TRIzol (Invitrogen) according to manufacturer's instructions. Single-pass cDNA was synthesized using the iScript cDNA synthesis kit (Bio-Rad, Hercules, Calif.). The quantitative real-time polymerase chain reaction (qRT-PCR) was performed using iQ SYBR Green Supermix (Bio-Rad). Human hepcidin and hemojuvelin mRNA concentrations were normalized to human glyceraldehyde 3-phosphate dehydrogenase (G3PD) or human β-actin. Human CEBPδ was used for IL-6 response positive control.

The following primers were used in qRT-PCR:

```
hepcidin:
forward:
5'-CACAACAGACGGGACAACTT-3';       (SEQ ID NO:8)

reverse:
5'-CGCAGCAGAAAATGCAGATG-3';       (SEQ ID NO:9)

hemojuvelin:
forward:
5'-CTCTTAGCTCCACTCCTTTCTG-3';     (SEQ ID NO:10)

reverse:
5'-GCCCTGCTTCCTTTAATGATTC-3';     (SEQ ID NO:11)

G3PD:
forward
5'-TGGTATCGTGGAAGGACTC-3';        (SEQ ID NO:12)

reverse:
5'-AGTAGAGGCAGGGATGATG-3';        (SEQ ID NO:13)

β-actin:
forward
5'-ATCGTGCGTGACATTAAG-3';         (SEQ ID NO:14)

reverse:
5'-ATTGCCAATGGTGATGAC-3';         (SEQ ID NO:15)

CEBPδ:
forward
5'-CAACGACCCATACCTCAG-3';         (SEQ ID NO:16)

reverse:
5'-GGTAAGTCCAGGCTGTAG-3'.         (SEQ ID NO:17)
```

Affymetrix HG-U133 Plus2 (Affymetrix, Santa Clara, Calif.) were used for microarray analysis according to manufacturer's protocol.

Western Blot Analysis and Antibody

Cellular protein was extracted with 150 mM NaCl, 10 mM EDTA, 10 mM Tris (pH 7.4) (NETT), 1% Triton X-100 and a protease inhibitor cocktail (Sigma-Aldrich, Saint Louis, Mo.) using methods known in the art. Frozen normal human liver fragments were pulverized in liquid nitrogen with a mortar and pestle. About 50 mg of tissue was homogenized in 700 μl NETT buffer, and about 150 μg of total protein extract was analyzed. Human sera and plasma samples were loaded directly at 1 or 2 μl/lane. Cell culture media were further processed before Western analysis. Serum-free conditioned cell culture media were concentrated by 5 kD molecular weight cut-off ultrafiltration with Amicon® Ultra-4 Centrifugal Filter Units (Millipore, Bedford, Mass.) using methods known in the art. Conditioned cell culture media that contained 30 μM Apo- and Holo-transferrin were extracted with the weak cation exchange matrix CM Macroprep (Bio-Rad, Richmond, Calif.), the matrix was eluted with 500 mM sodium chloride in 25 mM ammonium acetate buffer (pH 6.5), and the eluate was concentrated by ultrafiltration using methods known in the art. Conditioned cell culture media that contained 10% FBS were partially purified by cation exchange chromatography before concentration using methods known in the art. Protein samples were separated on 4-20% iGels (SDS-Tris-Glycine) (Gradipore, Hawthorne, N.Y.) with dithiothreitol (DTT) if not mentioned specifically otherwise, and silver-stained or transferred on Immobilon-P membrane (Millipore Corp., Bedford, Mass.) using methods known in the art.

Three different anti-hemojuvelin polyclonal antibodies were prepared by immunizing rabbits with peptide antigens: anti-G3pep2-2 and anti-G3pep2-3: Target sequence N-CRGDLAFHSAVHGIED-C, (SEQ ID NO:18) (1:1000); Ab112: Target sequence N-CDYEGRFSRLHGRPPG-C (SEQ ID NO:19) (1:5000). Western blots were visualized by chemiluminescence using methods known in the art.

Results

Suppression of Hemojuvelin mRNA Results in the Suppression of Hepcidin mRNA

Figure 1B:
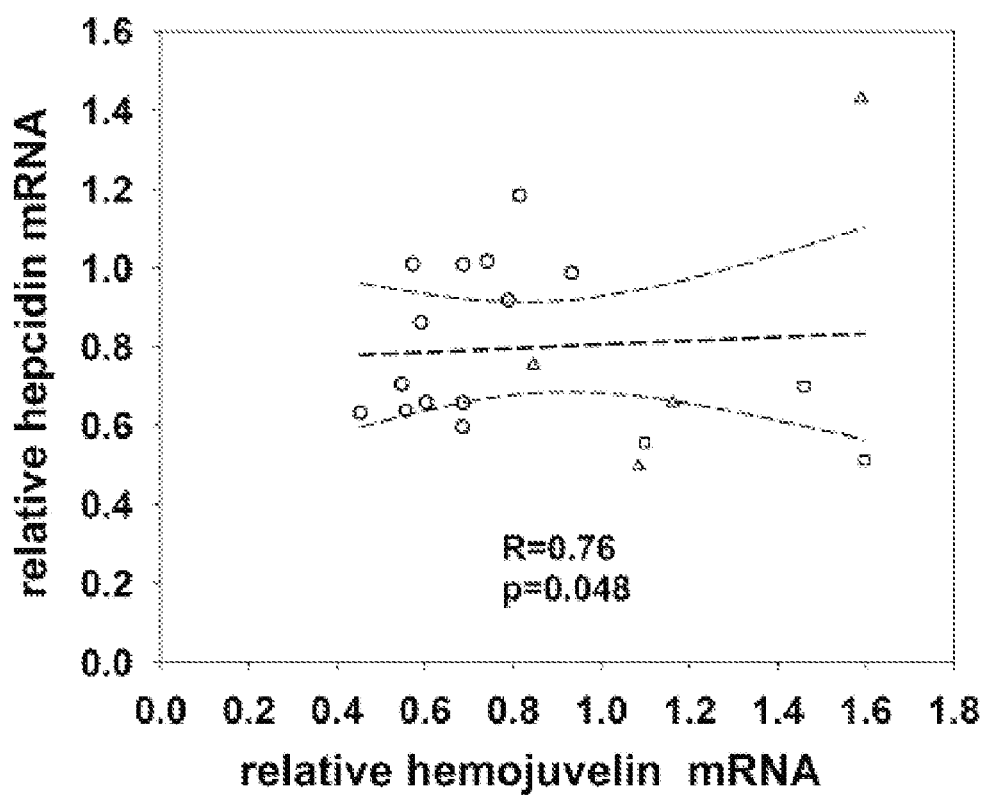

Four different siRNA sequences, HJVsi1, HJVsi2, HJVsi3, and HJVsi4, were used to target the coding and non-coding 3' untranslated (3'-UTR) regions of hemojuvelin mRNA. As shown in FIGS. 1A and 1B, each individual point represents an experiment in which Hep3B cells were treated with one of the siRNA preparations overnight, and then incubated for additional 24 hours before mRNA extraction. In each experiment, hemojuvelin and hepcidin mRNA were quantified by real time qRT-PCR and normalized to the housekeeping gene G3PD using methods known in the art. Control cells, NCsi1, NCsi2, and NCsi3, were treated only with transfection reagents and their hemojuvelin/G3PD and hepcidin/G3PD ratios were set as baseline=1. See FIG. 1B.

These siRNAs showed a wide range of efficiency (about 30% to about 90%) in suppressing hemojuvelin mRNA level about 48 hours after transfection. Decrease in hepcidin mRNA correlated with decreased hemojuvelin mRNA levels (R=0.64). See FIG. 1A. No significant suppression of hepcidin mRNA was observed when hemojuvelin mRNA concentration was above about 50% of untreated control. This is consistent with the observation that individuals with only one copy of disrupted HJV do not develop iron overload. See Papanikolaou, G., et al. (2004) Nat. Genet. 36:77-82, which is herein incorporated by reference. The 3 different siRNA negative controls showed slight suppression or induction of either hemojuvelin or hepcidin mRNA, but no significant correlation or specificity was observed as shown in FIG. 1B.

Hemojuvelin and IL-6 Independently Regulate Hepcidin mRNA

Figure 2:
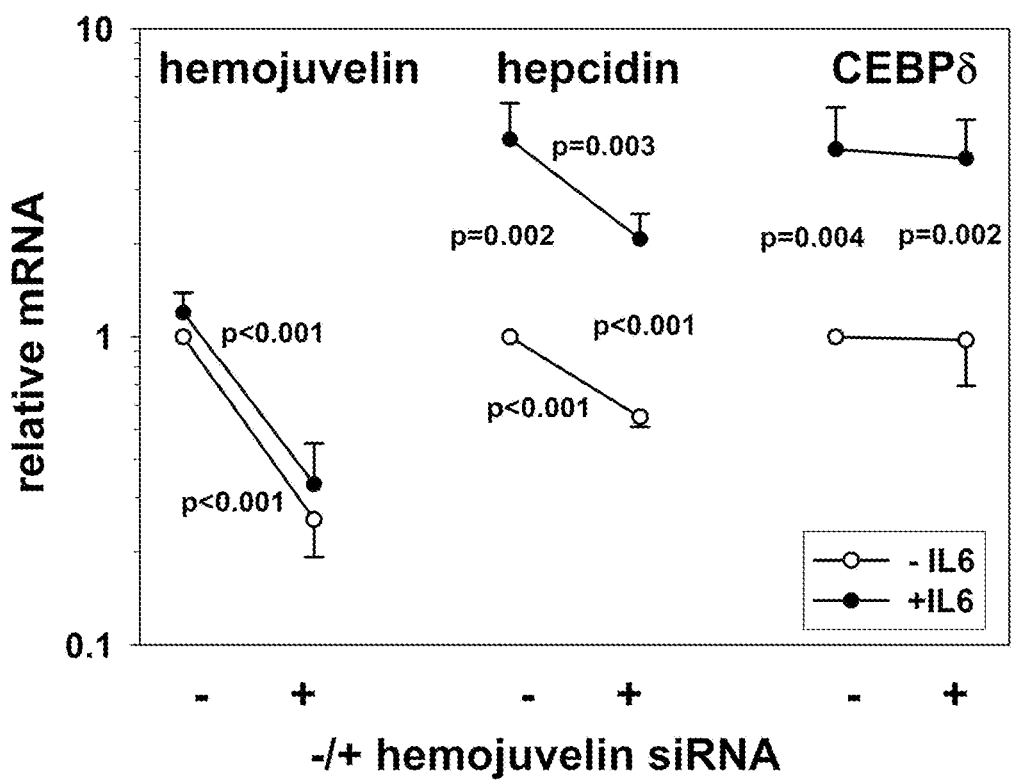
FIG. 2 is a graph showing hemojuvelin suppression decreased hepcidin expression but did not affect its inducibility by IL-6. Hep3B cells were first treated with hemojuvelin siRNA HJVsi3 (+) or diluent (−), followed by 20 ng/ml IL-6 (-●-) to induce hepcidin for 24 hours (n=6 separate experiments). Hepcidin mRNAs was assayed by qRT-PCR and normalized to G3PD. In each experiment, expression of each target/G3PD ratio in control cells (not treated with IL-6 or siRNA) was set as the baseline=1. Treatment with hemojuvelin siRNA significantly decreased both hemojuvelin and hepcidin mRNA levels in the presence and absence of IL-6, but did not affect mRNA expression of CEBPδ. Significant differences as judged by the paired Student t-test are indicated by their p values. Regardless of hemojuvelin siRNA treatment, IL-6 produced a similar fold induction of hepcidin and CEBPδ mRNA expression, indicating that the IL-6 effect is not modulated by hemojuvelin expression.

Next, whether hemojuvelin is necessary for the inflammatory induction of hepcidin was examined. IL-6 is a well-defined inducer of hepcidin during anemia of inflammation. See Nemeth, E., et al. (2004) J. Clin. Invest. 113:1271-1276, which is herein incorporated by reference. Hep3B cells were pretreated with hemojuvelin siRNA or diluent for 24 hours, followed by 24 hours of treatment with 20 ng/ml human IL-6 to induce hepcidin. See FIG. 2. Suppression of hemojuvelin to as low as about 10% to about 20% of the control (cells not treated with siRNA or IL-6) caused a maximum of about 2-fold reduction of hepcidin baseline expression, but did not interfere with its inducibility by IL-6 (a similar 4-fold induction of hepcidin mRNA level in both hemojuvelin siRNA treated and control cells). An IL-6 specific acute phase protein CEBPδ was used as a positive control for IL-6 induction as well as a negative control for hemojuvelin siRNA specificity. See Ramji, D. P., et al. (1993) Nucl. Acids Res. 21:289-294; and Alam, T., et al. (1992) J. Biol. Chem. 267:5021-5024, which are herein incorporated by reference. The mRNA levels of CEBPδ were unaffected by hemojuvelin siRNA treatment but were induced by approximately 4-fold with 20 ng/ml IL-6 in both hemojuvelin siRNA treated and control cells. These data showed that IL-6 and hemojuvelin act independently to regulate hepcidin mRNA levels.

Hemojuvelin Protein is Detected As Both Cell-Associated and Soluble Forms

Figure 3:
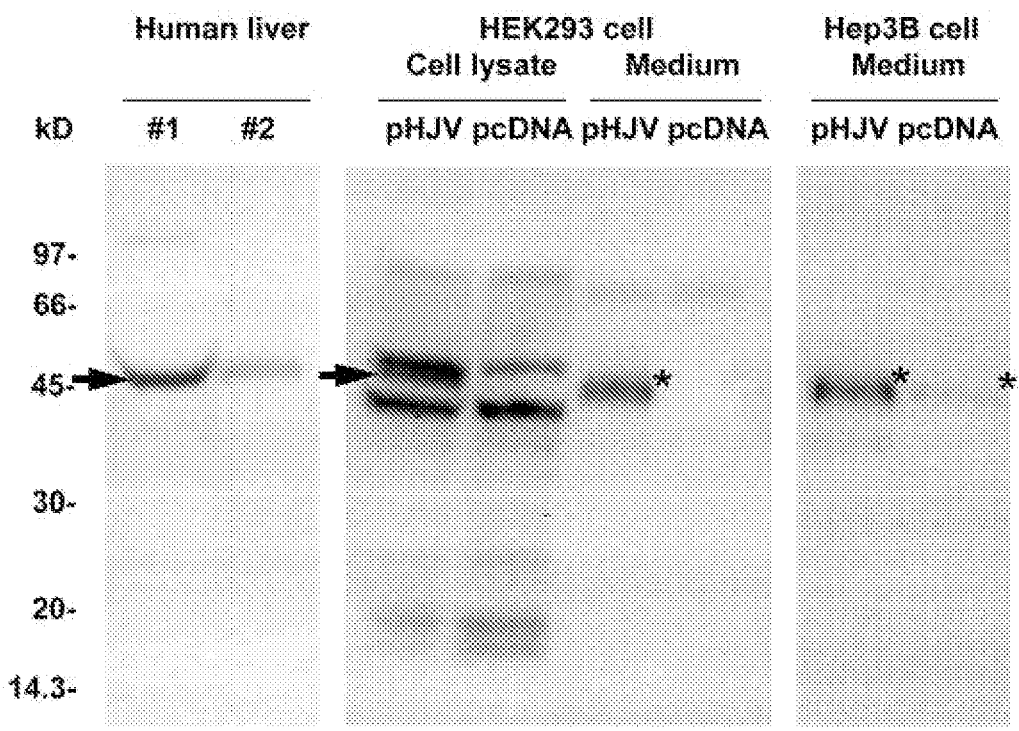
FIG. 3 shows gels evidencing that hemojuvelin protein exists in both cell-associated and soluble forms. HEK293 and Hep3B cells were transfected with pcDNA3.1 (+) or pcDNA-HJV in 6-well tissue culture plates and incubated overnight, followed by a 24-hour incubation in serum free medium (2 ml/well). Whole cell lysates were collected in 150 μl NETT buffer per well and 30 μl of cleared total protein solution was analyzed. Conditioned cell culture media (2 ml/sample) were filter concentrated (5 kD cutoff) and concentrates equivalent to 800 μl starting material were analyzed. Western blots after reducing SDS-PAGE were probed with anti-G3pep2-3 antibody. Arrows indicate cell-associated hemojuvelin (apparent MW=46 kD) in both human liver protein extracts (#1 and #2) and whole cell lysate of HEK293 cells transfected with pcDNA-HJV (pHJV), but not in HEK293 cells treated with control vector (pcDNA). Soluble hemojuvelin (apparent MW=44 kD) is indicated by "*", and seen in conditioned cell culture media from HEK293 and Hep3B cells transfected with pcDNA-HJV (pHJV), as well as in conditioned media from Hep3B cells transfected with control vector (pcDNA) but not in media from HEK293 cells treated with control vector (pcDNA).

Total protein extract from human liver was analyzed on reducing SDS-PAGE and the corresponding blot was probed with the polyclonal anti-hemojuvelin antibody anti-G3pep2-3 targeted to the N-terminus of hemojuvelin. One predominant protein band of about 46 kD was detected in human liver from 2 different donors. See FIG. 3, Lane 1 and 2. Lysate of Hep3B cells (with endogenous hemojuvelin mRNA expression), was also analyzed by western blot, but no signal was detected using any of the available antibodies (data not shown).

In order to confirm the specificity of antibody detection of the 46 kD protein band in human liver, the full length hemojuvelin cDNA was cloned into pcDNA 3.1 (+) vector to generate the pcDNA-HJV construct, and used it to transfect the Hep3B and HEK293T/17 (HEK293) cell lines (the latter with undetectable endogenous hemojuvelin mRNA) as positive controls for cellular expression of hemojuvelin. Hemojuvelin expression was compared in vector (pcDNA3.1 (+)) alone or in construct (pcDNA-HJV)-treated cells. Cell lysate and conditioned medium were analyzed by Western blot with anti-G3pep2-3. In cell lysate of HEK293 cells, a unique protein band of approximately 46 kD, identical in size to the band seen in human liver protein extract, was identified in pcDNA-HJV-treated cells but not in cells treated with control vector. See FIG. 3, Lane 3 and 4. No hemojuvelin-specific band was detected in the cell lysate of Hep3B cells transfected with pcDNA-HJV or pcDNA3.1 (+) (data not shown). This could be due to a low transfection efficiency in Hep3B cells (generally about 10%, compared to over 90% in HEL293T/17 cells, estimated by green fluorescence) and low detection sensitivity of anti-G3pep2-3 antibody.

Next, whether hemojuvelin was present in the media derived from cells expressing hemojuvelin was examined. In the conditioned culture medium of HEK293 cells transfected with pcDNA-HJV, but not with vector pcDNA 3.1 (+), one unique prominent protein band of approximately 44 kD was detected in Western blot using anti-G3pep2-3. See FIG. 3. A similar result with the conditioned culture medium of Hep3B cell transfected with both vectors was obtained. See FIG. 3. The detection of s-hemojuvelin in vector-treated Hep3B but not HEK293 cells is consistent with the endogenous hemojuvelin mRNA expression in Hep3B cells.

An alternative antibody Ab112, targeting a region 35 amino acids downstream from the region used to generate anti-G3pep2-3, detected both GPI-hemojuvelin and s-hemojuvelin in transfected Hep3B and HEK293 cells, but not in human liver. Using Ab112, under reducing conditions, an additional 16 kD reactive protein band was detected in both cell types but only one reactive protein band appeared under non-reducing conditions, 46 kD for GPI-hemojuvelin, and 44 kD for s-hemojuvelin (data not shown). There was about a 2 kD difference between the size of the GPI-hemojuvelin and s-hemojuvelin (46 kD vs 44 kD), indicating that a cleavage near the C-terminus of the cell-associated form caused the release of the soluble form.

Thus, GPI-hemojuvelin may be detected in human liver and in cultured cell lines engineered to express hemojuvelin. Moreover, s-hemojuvelin can also be detected in the media conditioned by cell lines expressing hemojuvelin.

Production of Recombinant Soluble Human Hemojuvelin (S-Hemojuvelin)

Figure 7:
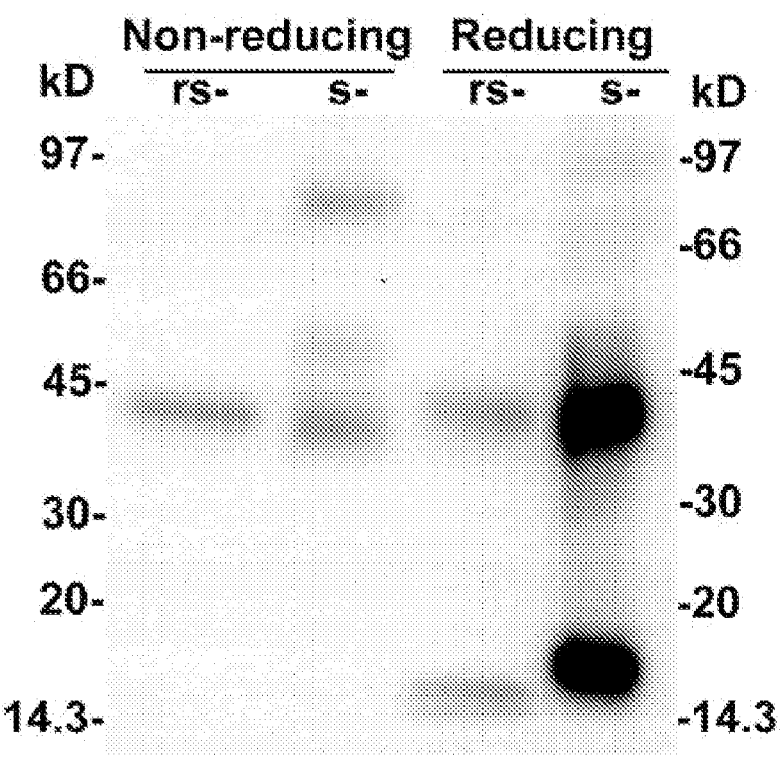
FIG. 7 is a gel evidencing that recombinant soluble hemojuvelin from baculovirus/insect cells is similar to that from mammalian cells, both in size and reactivity with antibodies. Soluble hemojuvelin was generated by transfecting HEK293 cells with pcDNA-HJV in 75 cm$^2$ flasks, 25 ml of conditioned cell culture medium (with 10% FBS) were harvested after a 40 hour incubation, then partially purified using cation exchange chromatography, desalted and concentrated by filtration (5 kD cutoff) to 250 μl soluble hemojuvelin standard (s-). Protein samples were loaded with or without reducing agent DTT, Western blot was then probed with Ab112. Purified s-hemojuvelin preparation (80 ng, rs-, Lane 1 and 3) showed similar reactive bands as the soluble hemojuvelin standard (5 μl, s-, Lane 2 and 4).
Figure 8:
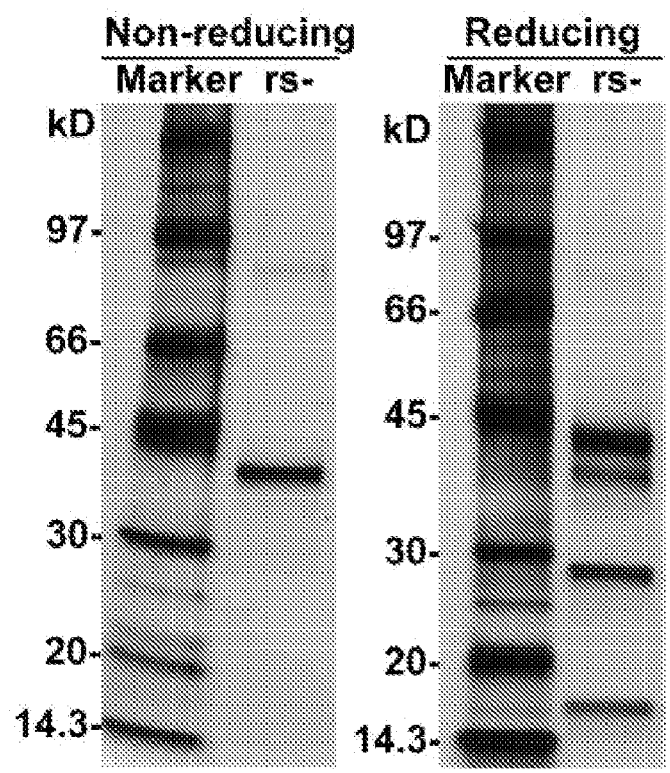
FIG. 8 shows gels indicating the purity of recombinant hemojuvelin. 500 ng of purified s-hemojuvelin was analysed on non-reducing and reducing SDS-PAGE, followed by silver staining. Purified s-hemojuvelin on non-reducing SDS-PAGE showed greater than about 95% purity (left panel). Reducing SDS-PAGE showed that purified s-hemojuvelin was partially cleaved into two major fragments of 16 kD and 29 kD. The 40 kD band in reducing SDS-PAGE (right panel) was identified by amino acid sequencing as the non-reduced form of s-hemojuvelin (identical migration as in non-reducing SDS-PAGE, left panel).

Recombinant soluble human hemojuvelin (s-hemojuvelin) was expressed in a baculovirus/insect cell expression system. Purified s-hemojuvelin migrated as a single band in western blots of non-reducing SDS-PAGE, but formed two bands in blots of reducing SDS-PAGE, reactive with anti-hemojuvelin antibody Ab112 (FIG. 7, Lane 1 and 3) but not with pre-immune serum (data not shown). The purified s-hemojuvelin was similar in size to s-hemojuvelin partially purified from HEK293 cell culture engineered to express hemojuvelin (FIG. 7, Lane 2, 4). The non-reducing SDS-PAGE gel staining indicated over 95% purity for s-hemojuvelin (FIG. 8, Lane 2). In addition to the full-length s-hemojuvelin (apparent MW of 44 kD), two additional bands of 29 kD and 16 kD (apparent MW) on reducing SDS PAGE (FIG. 8, Lane 4) were also observed. These two bands were not observed on a non-reducing SDS-PAGE (FIG. 8, Lane 2), suggesting that they were the proteolytic cleavage products of s-hemojuvelin linked together by a disulfide bond(s). Edman degradation was used to sequence the N-terminus of the two reduced fragments and non-reduced s-hemojuvelin. Undetectable signal indicated a characteristically blocked N-terminal glutamine at the start of the N-terminal fragment (amino acid 36Q). The C-terminal fragment generated the sequence PHVR . . . indicating that it was generated from an Asp-Pro cleavage site after amino acid 172D (FGD↓PHVR). Non-reduced s-hemojuvelin was also N-terminally blocked but generated a sequence suggestive of the exposure of a second N-terminus (PHVR) by cleavage. These results agree with previous report of three mouse RGMs (a, b, and c) and chicken RGM which all showed identical cleavage sites (FGD↓PH V/L R). See Niederkofler, V., et al. (2004) J. Neurosci. 24:808-818; and Monnier, P.P., et al. (2002) Nature 419:392-395, which are herein incorporated by reference. The conserved Asp-Pro bond is known to be unusually labile, and can undergo hydrolysis in acidic cellular compartments or after treatment with mild acids. See Lidell, M.E., et al. (2003) J. Biol. Chem. 278:13944-13951, which is herein incorporated by reference. The observation that s-hemojuvelin forms a disulfide-linked two chain structure with one blocked N-terminus explains the inconsistency between the apparent molecular weight and sequencing results previously interpreted as glycosylation and removal of the N-terminal fragment in native RGMs.

The unmodified hemojuvelin precursor protein (45.1 kD) could be subject to a series of post-translational modifications, due to the presence of an N-terminal signal peptide (3.57 kD), a C-terminal transmembrane motif characteristic for GPI anchor (2.46 kD), and multiple putative glycosylation and protease cleavage sites. After the removal of the signal peptide and C-terminal transmembrane domain, the s-hemojuvelin has a predicted MW of 39.1 kD. Mass spectrometry (MALDI-TOF) of s-hemojuvelin (apparent MW of 44 kD on SDS-PAGE) yielded a mass of about 41.5 kD with multiple peaks at about 160 D intervals, indicating a typical glycosylation pattern.

Soluble Hemojuvelin can be Detected in Human Plasma and Serum

Figure 4:
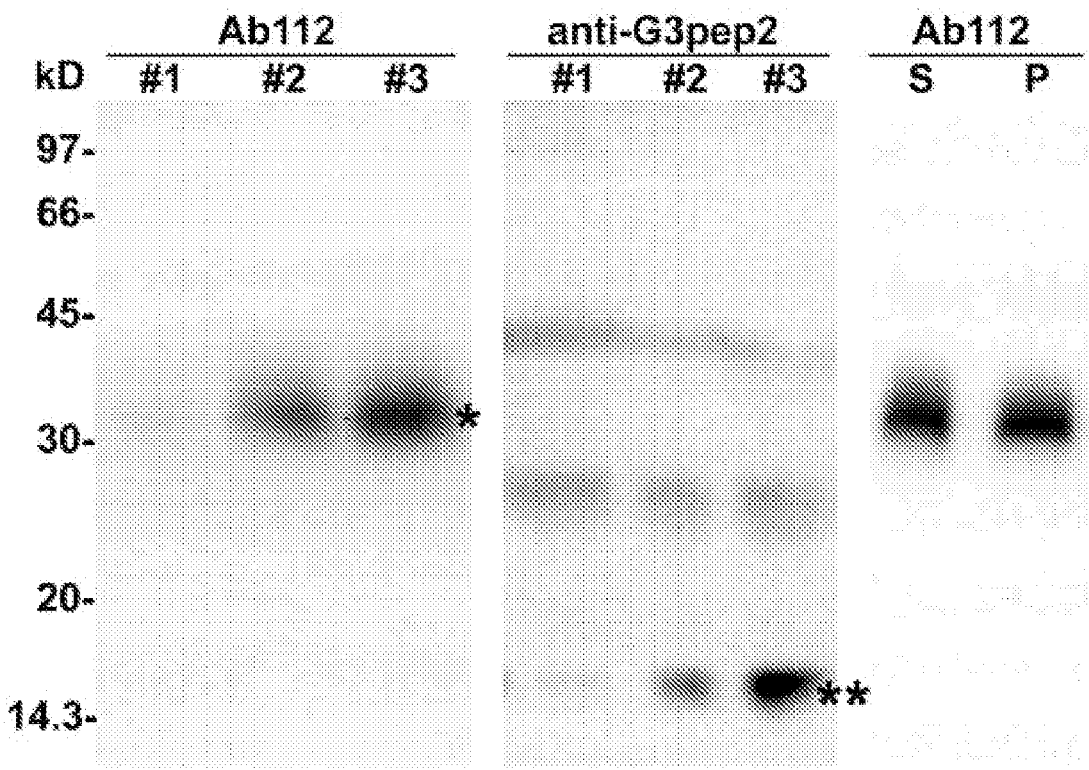
FIG. 4 shows gels evidencing that soluble hemojuvelin is present in human serum and plasma. Serum and plasma samples were separated on reducing SDS-PAGE. In Western blot analysis of all serum samples, Ab112 detected a protein band (*) of 30 kD (three different donors #1, #2, and #3, left panel), and anti-G3pep2-2 antibody detected a protein band (**) of 16 kD (middle panel). Pretreatment of Ab112 with excess s-hemojuvelin abolished the 30 kD Western blot signal. See FIG. 9. Blood plasma (1 μl, P, right panel) probed with Ab112 contained bands identical to those of serum from the same donor (1 μl, S, right panel) indicating that the hemojuvelin cleavage was not caused by the clotting reaction.
Figure 9:
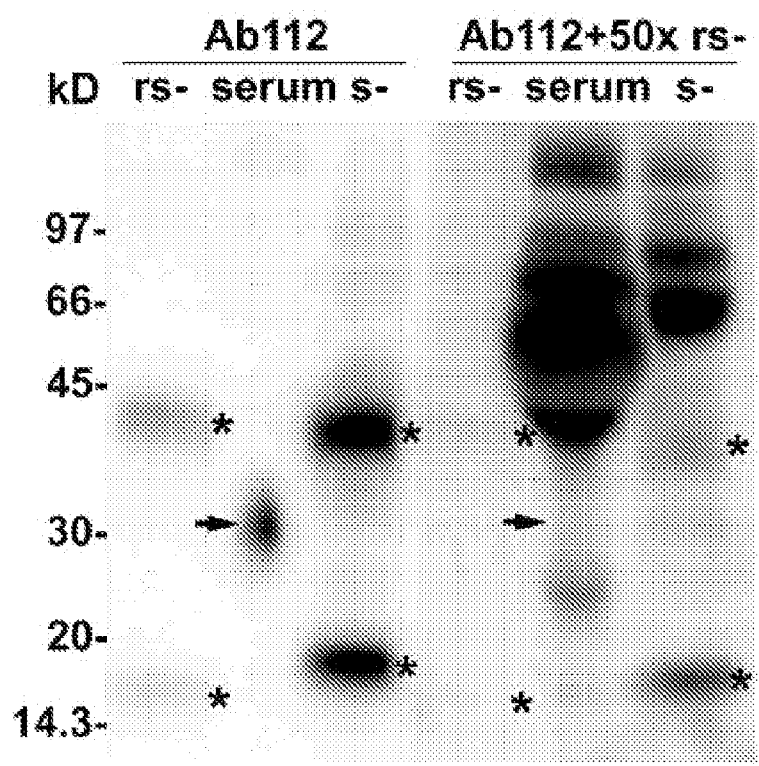
FIG. 9 shows gels indicating the specificity of soluble hemojuvelin detection in human serum. Ab112 antibody were diluted in antibody dilution buffer to final concentration (1:5000), and rotated at 4° C. overnight with or without about a 50-fold excess s-hemojuvelin (antigen/specific IgG ratio, 2.8 μg s-hemojuvelin/1 μl anti-serum). Two μl of human serum sample was loaded along with s-hemojuvelin (rs-, 50 ng) and soluble hemojuvelin standard (s-, 3 μl). One single blot was cut and probed in parallel with two antibody solutions. Arrows indicate that excess s-hemojuvelin completely abolished the 30 kD protein band in human serum. The hemojuvelin bands generated by engineered HEK293 and insect cells were also nearly abolished by antigen competition.

The release of s-hemojuvelin into cell culture indicated the possibility that s-hemojuvelin exists in vivo and has a physiological function. Two μl human serum was separated on a reducing SDS-PAGE and detected a single prominent protein band of 30 kD reactive with Ab112 (FIG. 4, left panel). Anti-G3pep2-2 antibody detected another specific protein band of 16 kD in the same samples (FIG. 4, middle panel, bottom bands). To confirm the 30 kD protein band is specific for hemojuvelin, Ab112 was neutralized with 50-fold excess of s-hemojuvelin (antigen/specific IgG ratio) and performed a western blot of human serum. The competition from excessive s-hemojuvelin completely abolished the 30 kD protein band in human serum (FIG. 9, Lane 2 and 5), as well as the bands corresponding to s-hemojuvelin (FIG. 9, Lane 1 and 4, rs-) and s-hemojuvelin from engineered HEK293 cells (FIG. 9, Lane 3 and 6, s-). In multiple serum samples, the relative signal intensity of the 30 kD band correlated well with the signal intensity of the 16 kD band, suggesting that they were both components of s-hemojuvelin in human serum.

To rule out the possibility that the cleavage of soluble human hemojuvelin in serum might be an artifact of the clotting process, 1 µl of human serum and plasma from the same donor on reducing SDS-PAGE probed with Ab112 was analyzed. The identical 30 kD protein band was detected in both human serum and plasma (FIG. 4, right panel), indicating the cleaved product is present in human blood.

The patterns of antibody reactivity of plasma hemojuvelin as compared to s-hemojuvelin (FIG. 9) indicated that the plasma hemojuvelin is cleaved between the two antigenic epitopes used for antibody generation rather than at the 172D↓P cleavage site of s-hemojuvelin downstream of the epitope region for Ab112.

The strong signal detected in human serum by western blot analysis indicates a substantial amount of s-hemojuvelin in human blood, estimated to be in the µg/ml range. Both the liver and the large mass of skeletal muscle may be the source of s-hemojuvelin, since both contain hemojuvelin mRNA at very high concentrations.

Figure 5A:
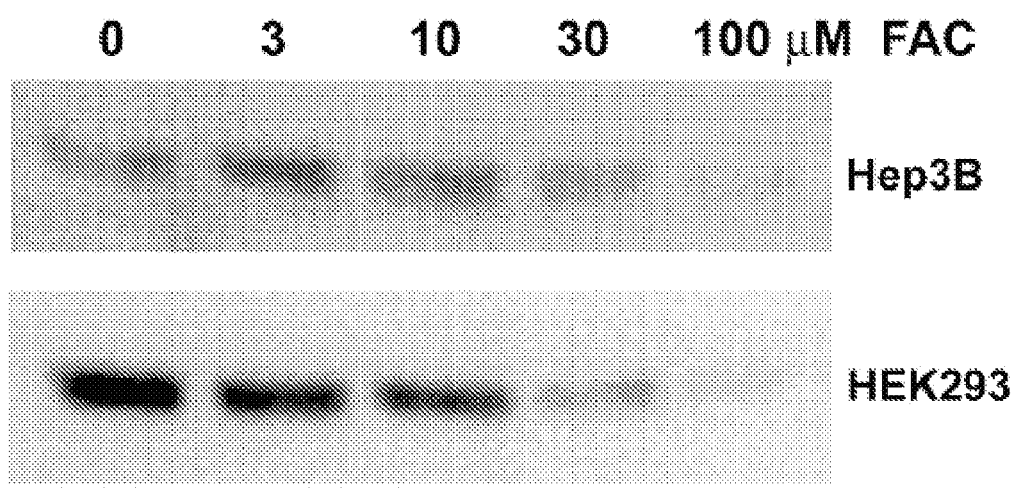
FIGS. 5A and 5B show that iron loading reduces soluble hemojuvelin release into cell culture medium. Each panel is representative of at least three independent experiments.
Figure 5B:
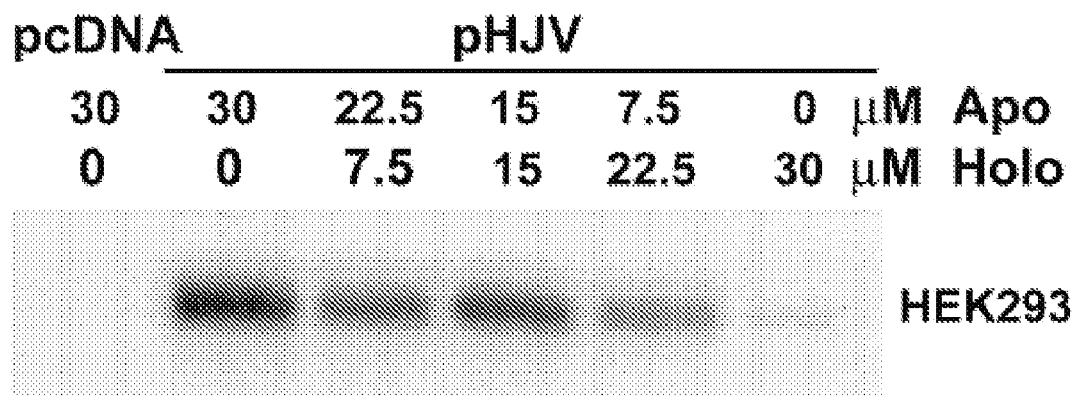

Iron Treatment Reduces the Amount of Soluble Hemojuvelin Released Into Cell Culture Medium To determine whether hemojuvelin protein expression or the release of soluble form is regulated by iron, ferric ammonium citrate (FAC) or apo/holo transferrin was added into cell cultures of both HEK293 and Hep3B cell line transfected with either pcDNA-HJV or vector alone. Western blot probed with anti-G3pep2-3 or Ab112 was used to analyze both whole cell lysate and conditioned cell culture medium. No significant change in cell-associated hemojuvelin could be detected (data not shown). However, s-hemojuvelin in cell culture media from both cell lines progressively decreased with increasing FAC concentration from 3 to 100 µM. See FIG. 5A. Similar results were also observed when treating hemojuvelin-transfected HEK293 cell with increasingly iron-saturated transferrin at a constant total transferrin concentration of 30 µM. See FIG. 5B.

Recombinant Soluble Hemojuvelin Suppresses Hepcidin mRNA in a Dose Dependent Manner in Cultured Primary Human Hepatocytes According to previous reports, the mRNA concentrations of hepatic RgmC (the HJV homolog in mouse) were not affected by iron feeding. See Krijt, J., et al. (2004) Blood 104:4308-4310, which is herein incorporated by reference. The inverse correlation of iron loading and s-hemojuvelin concentration in vitro leads to the hypothesis that s-hemojuvelin is a negative regulator of hepcidin mRNA concentration.

Figure 6:
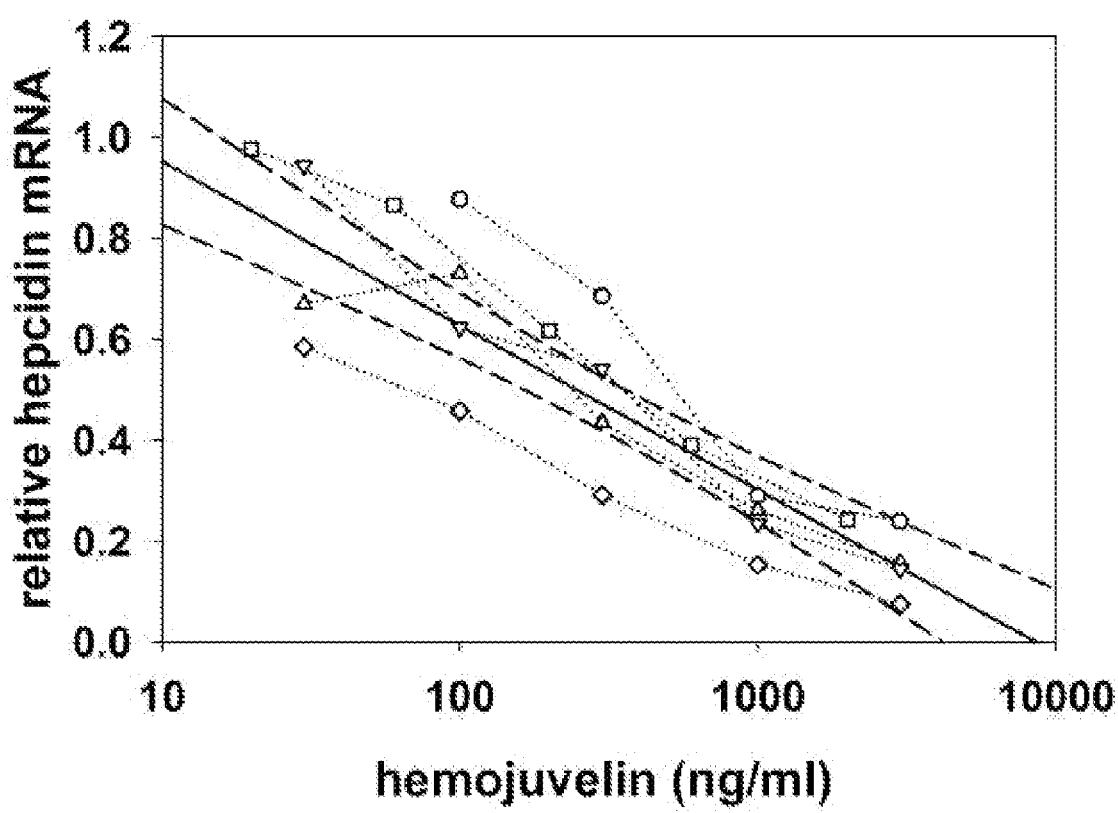
FIG. 6 is a graph showing dose-dependent suppression of hepcidin mRNA by s-hemojuvelin in primary human hepatocyte culture. Primary human hepatocyte cultures (n=5) from 4 different donors were treated for 24 hours with purified s-hemojuvelin from two different preparations. Hepcidin mRNA was quantified by real time qRT-PCR and normalized to the housekeeping gene β-actin. For each experiment, the hepcidin/β-actin ratio of untreated cells was considered as baseline=1. Individual experiments (open symbols, dotted lines) and the regression line with 95% confidence intervals are shown. Hepcidin mRNA expression showed a significant log-linear anti-correlation (R=−0.88, P<0.001) with added s-hemojuvelin concentration.

Considering the amount of s-hemojuvelin detectable on Western blot, the s-hemojuvelin protein level was estimated to be less than about 5 ng/ml in hepatocyte culture medium after a 24 hour incubation. Primary human hepatocytes were treated for 24 hours with higher concentrations of s-hemojuvelin (about 20 to 3000 ng/ml), similar to the concentrations detected in human sera, and observed that hepcidin mRNA concentrations decreased in a dose-dependent manner. No cytotoxicity was observed as judged by β-actin mRNA expression and cell morphology. The decrease in hepcidin mRNA level showed a striking log-linear anti-correlation with s-hemojuvelin concentration ($R^2>0.9$ in each individual experiment, data not shown), and this log-linear anti-correlation was consistent in hepatocyte cultures from 4 different donors and 2 independent preparations of s-hemojuvelin (FIG. 6), indicating a possible competition for a hemojuvelin ligand.

Figure 10A:
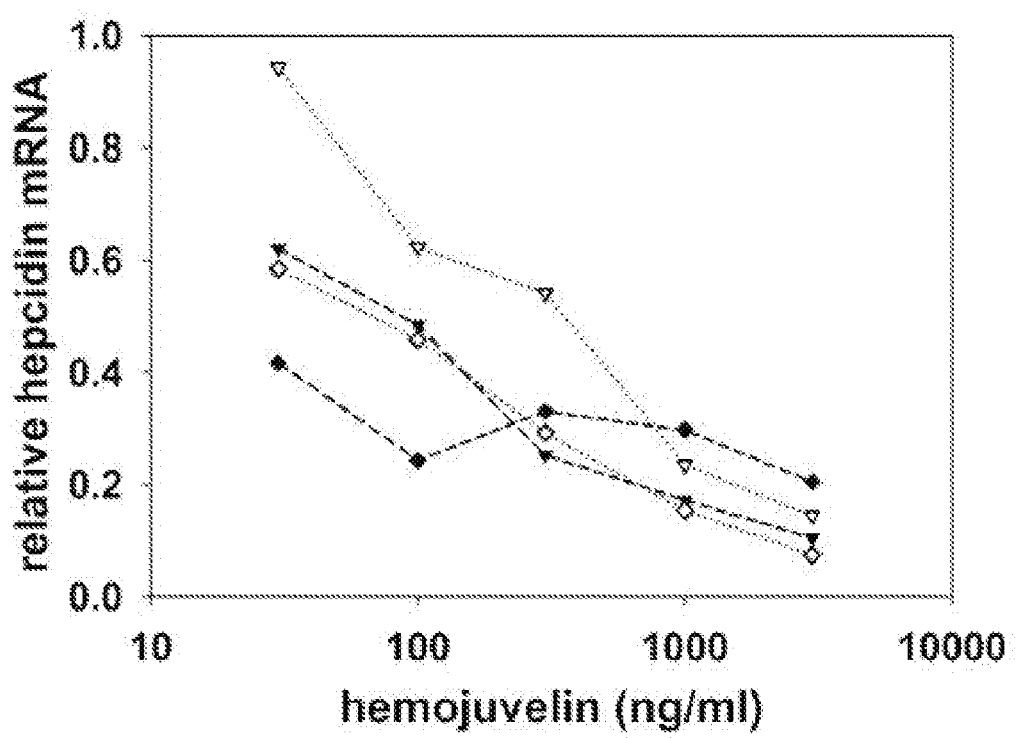
FIGS. 10A and 10B are graphs showing the combined effects of IL-6 and s-hemojuvelin on hepcidin mRNA. Primary human hepatocyte cultures from two different donors were treated for 24 hours with purified s-hemojuvelin and 20 ng/ml IL-6. Hepcidin mRNA was quantified by real time qRT-PCR and normalized to the housekeeping gene β-actin.
Figure 10B:
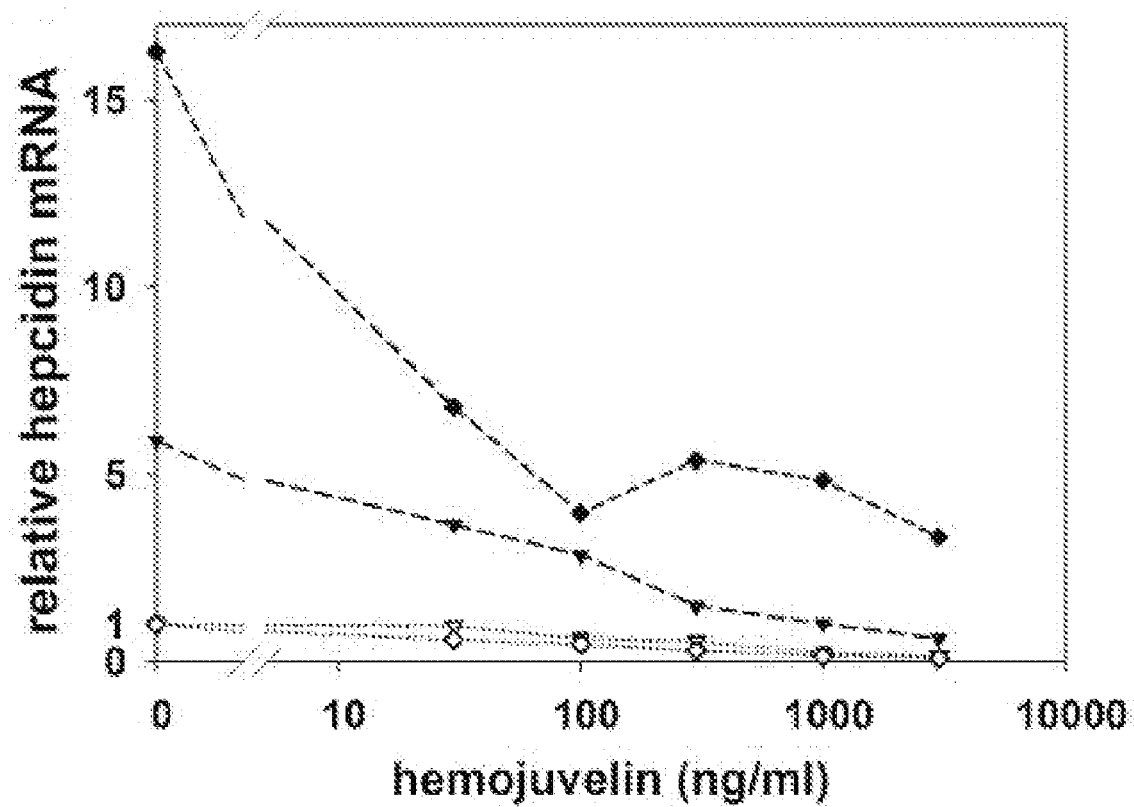

A similar dose-dependent fractional suppression of hepcidin mRNA by s-hemojuvelin in the presence of 20 ng/ml human IL-6 (FIG. 10A) was observed. This result indicated that the suppression of hepcidin mRNA expression was IL-6 independent, consistent with the observation from the hemojuvelin siRNA treatment that cell-associated hemojuvelin regulated hepcidin mRNA expression in an IL-6 independent manner. Nevertheless, treatment with high doses of s-hemojuvelin (about 1 to about 3 µg/ml) effectively reversed the 6 to 16-fold induction of hepcidin mRNA by 20 ng/ml of IL-6. See FIG. 10B. Therefore, the present invention provides methods of inhibiting, decreasing, or suppressing hepcidin in a subject which comprises administering to the subject s-hemojuvelin.

Figure 11A:
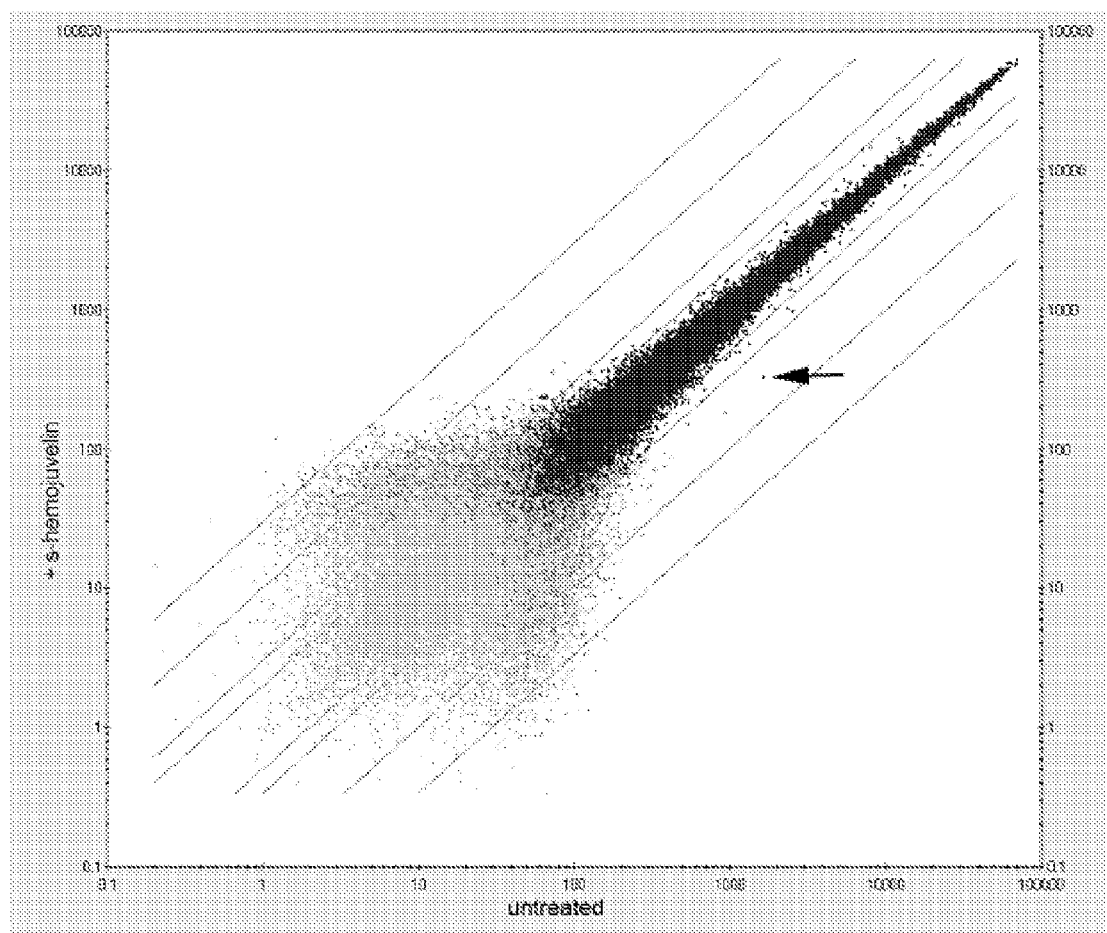
FIGS. 11A and 11B show two graphs indicating the effect of s-hemojuvelin on the global gene expression pattern in primary human hepatocytes. Each graph compares the gene expression in mock-treated cells with gene expression in s-hemojuvelin treated cells (3 μg/ml). Each dot represents a single spot on the array, corresponding to a single transcript. The dots on the diagonal represent genes whose expression is unchanged. The black arrow points to the dot representing the hepcidin transcript. The lines show 2-, 3-, 10- and 30-fold change.
Figure 11B:
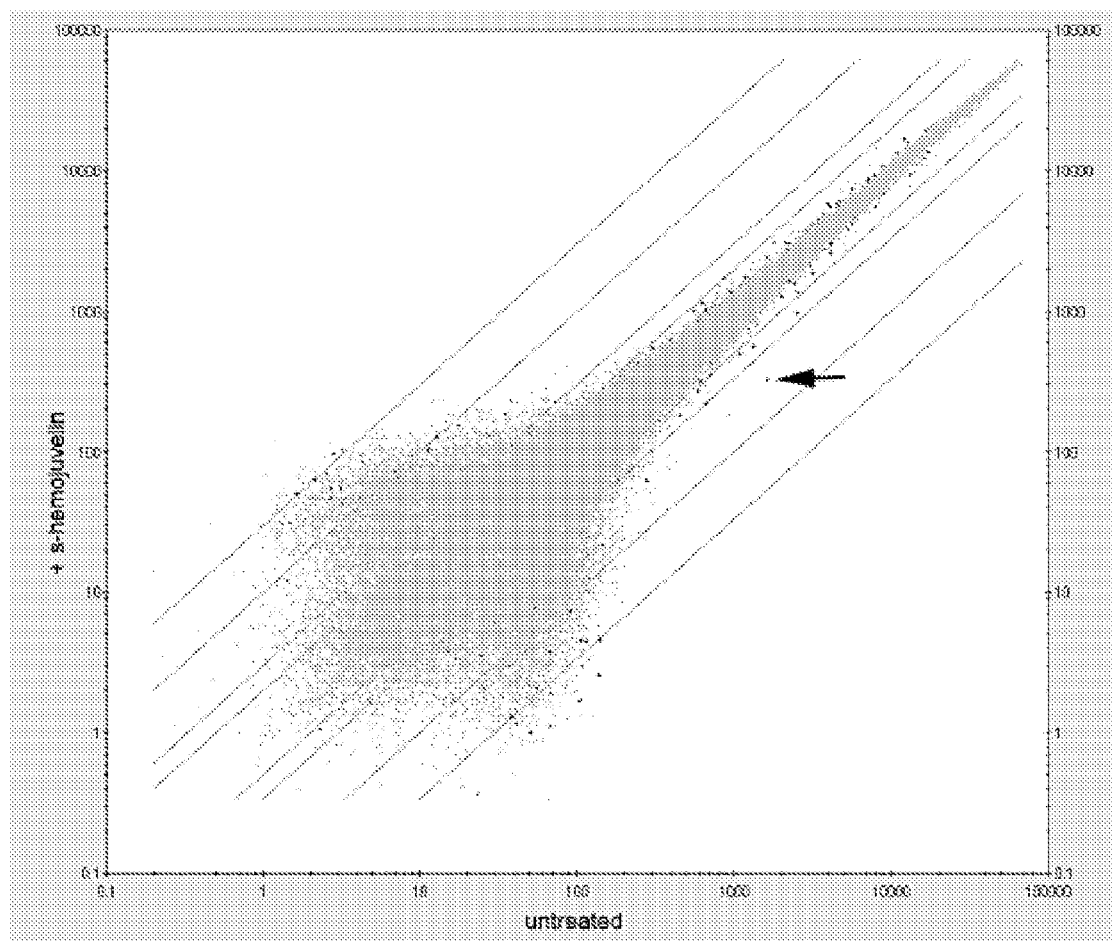

The suppression of hepcidin mRNA by s-hemojuvelin was highly selective. Using the Affymetrix HG-U133 Plus2 microarray, the global gene expression pattern in primary human hepatocytes treated with s-hemojuvelin (3 µg/ml) versus those treated with diluent (FIG. 11) was compared. Hepcidin mRNA decreased about 5-fold after treatment with s-hemojuvelin, the largest change of any transcript that was present in both treated and mock-treated hepatocytes. This decrease was significant at p<0.0001 using the statistics (at default settings) of the Affymetrix GeneChip Operating Software version 1.2.

Therefore, the present invention provides methods for regulating or modulating hepcidin expression or levels in subjects which comprises administering soluble hemojuvelin (s-hemojuvelin) to the subjects. As used herein, "soluble hemojuvelin" refers to natural and synthetic hemojuvelin proteins which lack the glycophosphatidylinositol (GPI) anchor that binds hemojuvelin to cell membranes. One of ordinary skill in the art may readily obtain s-hemojuvelin by removing the GPI anchor using methods known in the art, including protein cleavage and recombinant techniques. As used herein, the terms "protein", "polypeptide", and "peptide" are used interchangeably to refer to two or more amino acid residues linked together. Preferred s-hemojuvelin proteins of the present invention include polypeptides consisting of at least about 6, preferably at least about 20, and more preferably at least about 50 consecutive amino acid residues of SEQ ID NO:1. In some preferred embodiments, the s-hemojuvelin protein consists of SEQ ID NO:1. However, it is noted that other hemojuvelin proteins and fragments thereof known in the art, including those recited in U.S. Publication No. 20060073497, which is herein incorporated by reference, may be used in accordance with the present invention. Specifically, the hemojuvelin proteins and fragments known in the art may be engineered to lack the GPI anchor and used in accordance with the present invention. Therefore, as used herein, "soluble hemojuvelin" refers to hemojuvelin proteins and fragments thereof known in the art which lack a GPI anchor.

As used herein, a "disease of iron metabolism" includes diseases where aberrant iron metabolism directly causes the disease, or where iron blood levels are disregulated causing disease, or where iron disregulation is a consequence of another disease, or where diseases can be treated by modulating iron levels, and the like. More specifically, a disease of iron metabolism according to this disclosure includes iron overload disorders, iron deficiency disorders, disorders of iron biodistribution, other disorders of iron metabolism and other disorders potentially related to iron metabolism, etc.

Even more specifically diseases of iron metabolism includes hemochromatosis, ferroportin mutation hemochromatosis, transferrin receptor 2 mutation hemochromatosis, juvenile hemochromatosis, neonatal hemochromatosis, hepcidin deficiency, transfusional iron overload, thalassemia, thalassemia intermedia, alpha thalassemia, sideroblastic anemia, porphyria, porphyria cutanea tarda, African iron overload, hyperferritinemia, ceruloplasmin deficiency, atransferrinemia, congenital dyserythropoietic anemia, anemia of chronic disease, anemia, hypochromic microcytic anemia, iron-deficiency anemia, conditions with hepcidin excess, Friedreich ataxia, gracile syndrome, Hallervorden-Spatz disease, Wilson's disease, pulmonary hemosiderosis, hepatocellular carcinoma, cancer, hepatitis, cirrhosis of liver, pica, chronic renal failure, insulin resistance, diabetes, atherosclerosis, neurodegenerative disorders, multiple sclerosis, Parkinson's disease, Huntington's disease, Alzheimer's disease.

In some cases the diseases and disorders included in the definition of "disease of iron metabolism" are not typically identified as being iron related. It is recognized by the instant invention that based on the tissue distribution of HFE2A (hemojuvelin) and its related protein, hepcidin, that iron metabolism may play a significant role in these disease processes. For example, hepcidin is very highly expressed in the murine pancreas suggesting that diabetes (Type I or Type II), insulin resistance, glucose intolerance and other disorders may be ameliorated by treating underlying iron metabolism disorders. See Ilyin, G. et al. (2003) FEBS Lett. 542 22-26, which is herein incorporated by reference. As such, these diseases are encompassed under the broad definition. Those skilled in the art are readily able to determine whether a given disease is a "disease or iron metabolism" according to the present invention using methods known in the art, including the assays of WO 2004092405, which is herein incorporated by reference, and assays which monitor hepcidin, hemojuvelin, or iron levels and expression.

It is important to note that the various diseases of iron metabolism are caused by abnormal hepcidin production, either too much or too little. As provided herein, hepcidin production is regulated by hemojuvelin in such a way that GPI-hemojuvelin induces, increases, or stimulates hepcidin production and s-hemojuvelin suppresses, decreases, or inhibits hepcidin production.

Thus, the present invention provides methods for treating, preventing, or modulating diseases of iron metabolism in subjects which comprise administering to the subject GPI-hemojuvelin to increase hepcidin production or administering s-hemojuvelin to decrease hepcidin production. For example, to treat juvenile hemochromatosis in a subject, GPI-hemojuvelin is administered to the subject in order to increase hepcidin production. To treat anemia of chronic disease in a subject, s-hemojuvelin is administered to the subject in order to decrease hepcidin production.

The present invention also provides methods of monitoring or diagnosing diseases of iron metabolism in subjects which comprise assaying the levels of GPI-hemojuvelin, s-hemojuvelin, or both in the subject and determining whether the levels are normal or abnormal.

The present invention further provides compositions comprising the s-hemojuvelin proteins described herein. The compositions include pharmaceutical compositions which may be readily formulated for desired routes of administration using methods known in the art. Suitable formulations and pharmaceutically acceptable carriers are known in the art.

Expression of Soluble Hemojuvelin in Mice

Figure 12:
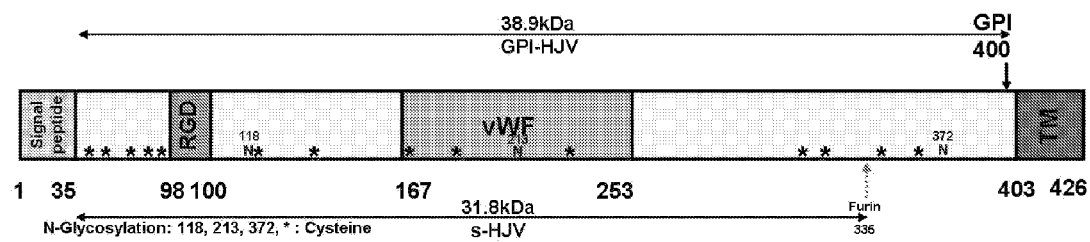
FIG. 12 shows human hemojuvelin protein sequence. Human hemojuvelin protein includes an N-terminal signal peptide (1-35), an RGD motif (98-100), a partial von Willebrand factor type D domain (167-253) and a glycosylphosphatidylinositol (GPI) anchoring site at the position of 400 followed by a c-terminal transmembrane motif required for GPI anchor formation.
Figure 13:
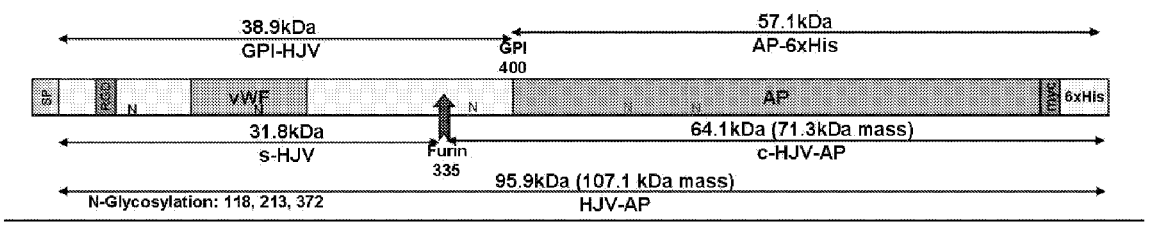
FIG. 13 shows human hemojuvelin-Alkaline phosphatase fusion protein. The c-terminus of human GPI-hemojuvelin (1-400) is fused with human placenta alkaline-phosphatase. Predicted molecular weight was indicated for each corresponding fragment. Molecular weights determined by mass-spectrometry were shown in brackets.

As provided herein an increased iron concentration (both ferric ammonium citrate and increasingly saturated iron transferrin) can suppress the release of soluble hemojuvelin into cell culture media in an in vitro system (HEK293 cells transfected with human hemojuvelin expressing vector). The release of soluble hemojuvelin is dependent on the enzymatic activity of furin convertase (encoded by FUR), which cleaved a conserved RXRR↓ site in hemojuvelin. See FIG. 12. This cleavage activity was sensitive to an inhibitor of furin convertase (Chloromethylketone). The cleavage site of soluble hemojuvelin was confirmed by amino-terminal sequencing of a human hemojuvelin-alkaline phosphatase fusion construct, which was processed into an N-terminal fragment with an identical migration pattern as soluble hemojuvelin. See FIG. 13.

On the other hand, purified human recombinant soluble hemojuvelin can suppress hepcidin mRNA expression in human primary hepatocyte cultures. This suppression had a strong dose-dependent log-linear anti-correlation with the added soluble hemojuvelin. This pattern is characteristic for a ligand-receptor competition model, where membrane associated hemojuvelin positively regulates hepcidin mRNA concentration in human liver, and soluble hemojuvelin acts as its natural antagonist. However, mouse primary hepatocyte cultures treated with purified human recombinant soluble hemojuvelin did not show downregulation of hepcidin mRNA expression. This could be due to the difference between mouse and human hemojuvelin (88.1% sequence identity in amino acid sequence). Tail vein injection of purified human recombinant soluble hemojuvelin in mice had no significant effect on hepatic hepcidin expression either.

To evaluate the physiological effect of soluble hemojuvelin in vivo, a lentiviral expression system for stable expression of soluble hemojuvelin in mouse liver and skeletal muscles was used. The expressed soluble hemojuvelin is expected to be released into circulation (based on observations in in vitro cell culture system using HEK293 cells).

Figure 14:
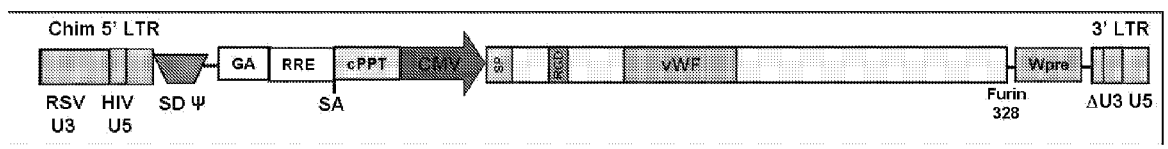
FIG. 14 shows mouse soluble hemojuvelin lentiviral expression transfer vector pRRL-Hjv-FUR While the above-identified drawings set forth preferred embodiments of the present invention, other embodiments of the present invention are also contemplated, as noted in the discussion. This disclosure presents illustrative embodiments of the present invention by way of representation and not limitation. Numerous other modifications and embodiments can be devised by those skilled in the art which fall within the scope and sprit of the principles of the present invention.

The lentiviral expression construct (Transfer vector pRRL-Hjv-FUR) express soluble hemojuvelin (s-Hjv) shown in FIG. 14 was constructed using methods known in the art.

The soluble mouse hemojuvelin protein sequence encoded by pRRL-Hjv-FUR is as follows:

MGQSPSPRSPHGSPPTLSTLTLLLLLCGQAHSQCKI (SEQ ID NO:20)

LRCNAEYVSSTLSLRGGGSPDTPRGGGRGGLASGGL

CRALRSYALCTRRTARTCRGDLAFHSAVHGIEDLMI

QHNCSRQGPTAPPPARGPALPGAGPAPLTPDPCDYE

ARFSRLHGRAPGFLHCASFGDPHVRSFHNQFHTCRV

QGAWPLLDNDFLFVQATSSPVSSGANATTIRKITII

FKNMQECIDQKVYQAEVDNLPAAFEDGSINGGDRPG

GSSLSIQTANLGSHVEIRAAYIGTTIIIRQTAGQLS

FSIRVAEDVARAFSAEQDLQLCVGGCPPSQRLSRSE

RNRR.

A control vector expressing mouse albumin (Transfer vector pRRL-Abl1) was also constructed using the same transfer vector. The lentiviral vectors may be packaged in a HEK293T cell line to generate replication incompetent viral particles and concentrated to prepare high titer viral supernatant. Subjects, such as C57BL/6 mice, are injected intravenously with $10^8$ viral particles/subject. All subjects are allowed sufficient time, e.g. 1 week, for transgene integration and to recover from virus induced inflammation before any further treatment. Then the effects of soluble hemojuvelin on hepatic hepcidin expression and body iron status are studied under the following physiological conditions:

1. Acute inflammation: induced by injecting turpentine into the interscapular fat pad.
2. Chronic inflammation: induced by injecting Cytodex beads co-cultured with *Staphylococcus epidermidis* (*S. Epi*) into the peritoneal cavity.
3. Dietary iron loading: by putting mice on moderate iron diet (50 ppm) through out experiment (before and after viral injection).
4. Acute iron ingestion: by switching experimental mice from low iron diet (<4ppm, before and after viral injection) to high iron diet (10000 ppm) for over night.

All mice are then euthanized. Then the levels of serum iron and transferrin saturation, hepatic hepcidin, hemojuvelin, soluble hemojuvelin, CEBP/delta, IL-6 mRNA, skeletal muscle hemojuvelin, beta-actin mRNA, transgene genome insertion are measured using qRT-PCR. The level of plasma soluble hemojuvelin protein may also be measured using ELISA.

To the extent necessary to understand or complete the disclosure of the present invention, all publications, patents, and patent applications mentioned herein are expressly incorporated by reference therein to the same extent as though each were individually so incorporated.

Variations, modification, and other implementations of what is described herein will occur to those of skill in the art without departing from the spirit and scope of the invention and the following claims.

What is claimed is:

1. A method of treating, a disease of iron metabolism in a mammalian subject diagnosed as having the disease of iron metabolism which comprises administering to the mammalian subject a therapeutically effective amount of at least one mammalian soluble hemojuvelin protein.

2. The method of claim 1, wherein the soluble hemojuvelin protein lacks its glycophosphatidylinositol anchor.

3. The method of claim 1, wherein the soluble hemojuvelin protein consists of SEQ ID NO:1.

4. The method of claim 1, wherein the disease of iron metabolism is anemia of chronic disease, juvenile hemochromatosis, adult onset hemochromatosis, iron overload, and iron deficiency anemia.

* * * * *

UNITED STATES PATENT AND TRADEMARK OFFICE
CERTIFICATE OF CORRECTION

| | |
|---|---|
| PATENT NO. | : 7,534,764 B2 |
| APPLICATION NO. | : 11/427095 |
| DATED | : May 19, 2009 |
| INVENTOR(S) | : Ganz |

Page 1 of 1

It is certified that error appears in the above-identified patent and that said Letters Patent is hereby corrected as shown below:

In the Claims:

In col. 27, claim 1, line 9, please change "treating, a" to --treating a--.

In col. 28, claim 4, line 12, please change "and" to --or--.

Signed and Sealed this
Seventeenth Day of September, 2013

Teresa Stanek Rea
*Deputy Director of the United StatesPatent and Trademark Office*